United States Patent [19]

Nagata et al.

[11] Patent Number: 5,536,878
[45] Date of Patent: Jul. 16, 1996

[54] METHOD FOR PREPARING AROMATIC SECONDARY AMINO COMPOUND

[75] Inventors: Teruyuki Nagata, Ohmuta; Chiyuki Kusuda, Kumamoto-ken; Masaru Wada, Ohmuta; Kenichi Satou, Mobara; Masae Uchida, Ohmuta, all of Japan

[73] Assignee: Mitsui Toatsu Chemicals, Inc., Tokyo, Japan

[21] Appl. No.: 353,379

[22] Filed: Dec. 2, 1994

Related U.S. Application Data

[60] Continuation-in-part of Ser. No. 287,273, Aug. 8, 1994, abandoned, which is a division of Ser. No. 100,149, Aug. 2, 1993, Pat. No. 5,382,690.

[30] Foreign Application Priority Data

| Aug. 11, 1992 | [JP] | Japan | 4-214078 |
| Sep. 30, 1992 | [JP] | Japan | 4-261505 |
| Oct. 5, 1992 | [JP] | Japan | 4-265897 |
| Oct. 5, 1992 | [JP] | Japan | 4-265898 |
| Oct. 21, 1992 | [JP] | Japan | 4-282940 |
| Oct. 28, 1992 | [JP] | Japan | 4-290133 |
| Oct. 29, 1992 | [JP] | Japan | 4-291311 |
| Nov. 6, 1992 | [JP] | Japan | 4-297096 |
| May 21, 1993 | [JP] | Japan | 5-119975 |
| May 24, 1993 | [JP] | Japan | 5-121423 |
| May 26, 1993 | [JP] | Japan | 5-124062 |
| May 28, 1993 | [JP] | Japan | 5-126826 |
| May 28, 1993 | [JP] | Japan | 5-126827 |
| Jun. 3, 1993 | [JP] | Japan | 5-133273 |
| Dec. 3, 1993 | [JP] | Japan | 5-303707 |
| Dec. 8, 1993 | [JP] | Japan | 5-307638 |
| Apr. 11, 1994 | [JP] | Japan | 6-071734 |

[51] Int. Cl.$^6$ .............................. C07C 209/24
[52] U.S. Cl. ............... 564/396; 564/385; 564/391; 564/397; 564/415; 562/443; 562/458; 549/480; 549/492
[58] Field of Search .................... 564/389, 391, 564/396, 397

[56] References Cited

U.S. PATENT DOCUMENTS

| 5,344,987 | 9/1994 | Immel et al. | 564/435 |
| 5,449,829 | 9/1995 | Kusuda et al. | 564/397 |

FOREIGN PATENT DOCUMENTS 5-117214  5/1993  Japan.

*Primary Examiner*—Richard L. Raymond
*Attorney, Agent, or Firm*—Burns, Doane, Swecker, & Mathis

[57] ABSTRACT

Disclosed are (1) a method for preparing an aromatic secondary amino compound which comprises reacting an N-cyclohexylideneamino compound in the presence of a hydrogen moving catalyst and a hydrogen acceptor by the use of a sulfur-free polar solvent and/or a cocatalyst, and (2) a method for preparing an aromatic secondary amino compound which comprises reacting cyclohexanone or a nucleus-substituted cyclohexanone, an amine and a nitro compound corresponding to the amine in a sulfur-free polar solvent in the presence of a hydrogen moving catalyst, a cocatalyst being added or not added. In a further aspect, a method is provided for the preparation of aminodiphenylamine by reacting phenylenediamine and cyclohexanone in the presence of a hydrogen transfer catalyst in a sulfur-free polar solvent while using nitroaniline as a hydrogen acceptor.

8 Claims, No Drawings

METHOD FOR PREPARING AROMATIC SECONDARY AMINO COMPOUND

CROSS-REFERENCE TO RELATED APPLICATIONS

This application is a continuation-in-part of application Ser. No. 08/287,273, filed on Aug. 8, 1994, now abandoned, which is a divisional of application Ser. No. 08/100,149 filed on Aug. 2, 1993, now U.S. Pat. No. 5,382,690.

BACKGROUND OF THE INVENTION (a) Field of the Invention

The present invention relates to an improved method for preparing an aromatic secondary amino compound. The present invention also relates to an improved method for the preparation of aminodiphenylamine.

The aromatic secondary amino compound obtained by the method of the present invention is an extremely important industrial chemical such as a raw material for rubber chemicals, dyes and the like.

(b) Description of the Prior Art

As methods for preparing an aromatic secondary amino compound, there are known a method in which the reaction of toluidine is carried out in a liquid phase at 300° to 400° C. in the presence of a suitable self-condensation type reaction catalyst ($BF_3$, $FeCl_2$, a salt of an ammonium halogenide, or a mineral acid), and a method in which cresol is reacted with toluidine at 330° to 340° C. under pressure in the presence of triphenyl phosphate.

Other methods for preparing the aromatic secondary amino compound are also known which comprise the dehydrogenation reaction of an N-cyclohexylideneamino compound. For example, there are a method for obtaining N-cyclohexylidene-N'-isopropylphenylenediamine at a temperature of 350° C. or less in the presence of a dehydrogenation catalyst (British Patent No. 989257); a method in which reaction is carried out in a gaseous phase, while oxygen or an oxygen-containing gas is fed at 300° to 450° C. in the presence of an oxidizing catalyst such as silica or alumina (Japanese Patent Application Laid-open No. 49924/1974); a method for obtaining 4-methyldiphenylamine by reaction at 300° to 500° C. in the presence of a dehydrogenation catalyst selected from the group consisting of nickel, platinum, palladium and copper-chromium alloy (Japanese Patent Application Laid-open No. 49925/1974); and a method for preparing an amino compound by the use of a specific nickel/chromium catalyst (Japanese Patent Publication No. 4623/1982).

Still other methods are already known in which a nitro compound is used as a hydrogen acceptor in the presence of a hydrogen moving catalyst to produce an amine in the system, and a nucleus-substituted cyclohexanone is simultaneously reacted with the amine to prepare an aromatic secondary amino compound. For example, there are a method for obtaining p-ethoxydiphenylamine by reacting p-nitrophenetole with a large excess of cyclohexanone in the presence of a palladium catalyst (British Patent No. 975097); a method for obtaining 2,6-dimethyldiphenylamine by reacting ⅓ mol of 2,6-dimethylaniline, ⅔ mol of 2,6-dimethylnitrobenzene, and cyclohexanone in the presence of a palladium catalyst, the amount of cyclohexanone being 10% in excess of the total of 2,6-dimethylaniline and 2,6-dimethylnitrobenzene (British Patent No. 989257); and a method for preparing a diphenylamine derivative by reacting 2-(alkyl or alkoxy)-4-alkoxynitrobenzene, 2-(alkyl or alkoxy)-4-alkoxyaniline and cyclohexanone in the presence of a palladium catalyst (Japanese Patent Application Laid-open No. 117214/1993).

However, these conventional methods have drawbacks of (1) severe reaction conditions, (2) a low reaction rate, and (3) a low yield. For these reasons, they are not industrially satisfactory manufacturing methods.

Known preparation processes of 4-aminodiphenyl-amine include rearrangement and reduction of N-nitroso-diphenylamine obtained by nitrosation of p-phenylenediamine (P.B. Reports 77764, 27–32) and condensation of formanilide or acetanilide with a halonitrobenzene, followed by reduction of the nitro group [Journal of Organic Chemistry, 42(10), 1786–90]. Known preparation processes of 2-aminodiphenylamine include rearrangement of an azo compound [Journal of Organic Chemistry, 295(1), 91–7, 1985]. Further, known preparation processes of 3-aminodiphenylamine include reduction of 3-nitrodiphenylamine. They are however hardly considered as industrially advantageous processes, because they require a complex reaction step, a large amount of a special reagent and/or solvent, and/or a precise purification step.

It is also known, as in the further aspect of the present invention, to prepare aminodiphenylamine by reacting cyclohexanone and phenylenediamine in the presence of a hydrogen transfer catalyst and a hydrogen receptor. Pursuant to this process, aminodiphenylamine has been obtained by reacting cyclohexanone and phenylenediamine in the presence of a palladium catalyst while using α-methylstyrene as a hydrogen receptor (Japanese Patent Laid-Open No. 58648/1982). In this process, however, except for its use as a hydrogen receptor, α-methylstyrene cannot effectively be used for the reaction, in contrast with the hydrogen receptor in this further aspect of the present invention, and phenylenediamine as a raw material has to be supplied in its entirety into the reaction system in the form of phenylenediamine. The reaction has to be conducted at elevated temperature and pressure. This process is therefore hardly considered to be satisfactory as an industrial process.

SUMMARY OF THE INVENTION

An object of the present invention is to provide an industrially improved method for preparing an aromatic secondary amino compound from an N-cyclohexylidene amino compound or cyclohexanone (inclusive of a nucleus-substituted compound), and according to this method, the above-mentioned problems can be solved.

As a result of various investigations, it has been found that the aromatic secondary amino compound can be obtained under extremely moderate conditions in a high yield by (1) using a sulfur-free polar solvent and/or a cocatalyst at the time of the dehydrogenation reaction of an N-cyclohexylideneamino compound in the presence of a hydrogen moving catalyst and a hydrogen acceptor, or (2) reacting cyclohexanone or a nucleus-substituted cyclohexanone with an amine in a sulfur-free polar solvent in the presence of a hydrogen moving catalyst by the use of a nitro compound corresponding to the amine as a hydrogen acceptor, or adding a specific cocatalyst to this system and then reacting the same. In consequence, one aspect of the present invention has been attained.

In accordance with a further object, it has been found that upon reaction of phenylenediamine and cyclohexanone in the presence of a hydrogen transfer catalyst in a sulfur-free polar solvent, use of nitroaniline as a hydrogen receptor makes it possible to obtain aminodiphenylamine in a high yield under extremely mild conditions and further to use as a raw material phenylenediamine formed from nitroaniline in the reaction system, leading to the present invention.

Therefore, in a further aspect of the present invention, there is thus provided a method for the preparation of aminodiphenylamine, which comprises reacting phenylenediamine and cyclohexanone in the presence of a hydrogen transfer catalyst in a sulfur-free polar solvent while using nitroaniline as a hydrogen acceptor.

According to the method of the further aspect of the present invention, aminodiphenylamine can be obtained in a high yield under extremely mild conditions. Additionally, phenylenediamine formed from nitroaniline can be used as a raw material in the reaction system and at the same time, any surplus portion of phenylenediamine can be reused together with the catalyst.

DETAILED DESCRIPTION OF THE PREFERRED EMBODIMENTS

The first aspect of the present invention is directed to a method for preparing an aromatic secondary amino compound represented by the formula (2)

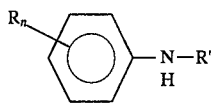 (2)

wherein each R is a hydrogen atom, alkyl group, alkoxy group, amino group, hydroxyl group or fluorine; n is an integer of from 0 to 5; and R' is an alkyl group, phenyl group, benzyl group, naphthyl group, furyl group, furfuryl group or cyclohexyl group, and R' may be substituted by an alkyl group, alkoxy group, phenyl group, phenoxy group, cyclohexyl group, amino group, substituted amino group, carboxyl group, hydroxyl group or fluorine which comprises the step of subjecting, to a dehydrogenation reaction, an N-cyclohexylideneamino compound represented by the formula (1)

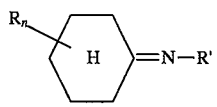

wherein R, R' and n are defined above in the presence of a hydrogen moving catalyst and a hydrogen acceptor, said method being characterized in that a sulfur-free polar solvent is used at the time of the dehydrogenation reaction.

The N-cyclohexylideneamino compound which is used as a starting material can be easily synthesized from an amine (or its derivative having an amino group with a substituent) and cyclohexanone or its derivative in accordance with a known process.

Examples of the alkyl group represented by R in the formula (1) include methyl, ethyl, propyl, isopropyl, butyl, isobutyl, tert-butyl, pentyl, phenylmethyl, amino-methyl, hydroxymethyl and fluoromethyl, and above all, methyl and ethyl are preferable.

Examples of the alkoxy group include methoxy, ethoxy, butoxy, pentyloxy, hexyloxy, heptyloxy, octyloxy, nonyloxy, decyloxy, dodecyloxy, hexadecyloxy, aminomethoxy and fluoromethoxy, and above all, methyloxy, ethyloxy are preferable.

Examples of the amino group include amino, methylamino, ethylamino, propylamino, isopropylamino, butylamino, isobutylamino, tert-butylamino, pentylamino, dimethylamino, diethylamino, cyclohexylamino and acetylamino.

Examples of the alkyl group represented by R' in the formula (1) include methyl, ethyl, propyl, isopropyl, butyl, isobutyl, tert-butyl, aminomethyl, aminoethyl, aminopropyl, 2-aminopropyl, 3-aminopropyl, aminobutyl and hydoxyethyl.

Examples of the phenyl group include phenyl, o-methylphenyl, m-methylphenyl, p-methylphenyl, p-ethyl-phenyl, p-propylphenyl, p-isopropylphenyl, p-butylphenyl, p-tert-butylphenyl, p-pentylphenyl, p-hexylphenyl, p-heptylphenyl, p-octylphenyl, p-nonylphenyl, p-decyl-phenyl, p-dodecylphenyl, p-hexadecylphenyl, 3,4-dimethylphenyl, 2,3-dimethylphenyl, 2,6-dimethylphenyl, 2,4,6-trimethylphenyl, p-methoxyphenyl, p-ethoxyphenyl, p-butoxyphenyl, p-pentyloxyphenyl, p-hexyloxyphenyl, p-heptyloxyphenyl, p-octyloxyphenyl, p-nonyloxyphenyl, p-phenyloxyphenyl, p-trioxyphenyl, p-acetylphenyl, p-benzoylphenyl, p-aminophenyl, m-aminophenyl, p-methylaminophenyl, p-ethylaminophenyl, p-butylaminophenyl, p-tert-butyl-aminophenyl, p-octylaminophenyl, p-dodecylaminophenyl, p-cyclohexylphenyl, p-methylcyclohexylphenyl, p-ethyl-cyclohexylphenyl, p-propylcyclohexylphenyl, p-hydroxy-phenyl, p-carboxyphenyl and p-fluorophenyl, and phenyl and p-methylphenyl are preferable.

Examples of the benzyl group include benzyl, o-methylbenzyl, m-methylbenzyl, p-methylbenzyl, p-ethylbenzyl, p-propylbenzyl, p-isopropylbenzyl, p-butylbenzyl, p-tert-butylbenzyl, p-pentylbenzyl, p-hexylbenzyl, p-heptylbenzyl, p-octylbenzyl, p-nonylbenzyl, p-decylbenzyl, p-dodecylbenzyl, p-hexadecylbenzyl, p-acetylbenzyl, 3,4-dimethylbenzyl, 2,3-dimethylbenzyl, 2,6-dimethylbenzyl, 2,4,6-trimethylbenzyl, p-methoxybenzyl, p-ethoxybenzyl, p-butoxybenzyl, p-pentyloxybenzyl, p-hexyloxybenzyl, p-heptyloxybenzyl, p-octyloxybenzyl, p-nonyloxybenzyl, p-phenyloxybenzyl, p-tolyloxybenzyl, p-benzoylbenzyl, p-methylaminobenzyl, p-ethylaminobenzyl, p-butylaminobenzyl, p-tert-butylaminobenzyl, p-octylaminobenzyl, p-dodecylaminobenzyl, p-cyclohexylbenzyl, p-methylcyclohexylbenzyl, p-ethylcyclohexylbenzyl, p-propylcyclohexylbenzyl, p-hydroxybenzyl, p-carboxybenzyl and p-fluorobenzyl.

Examples of the cyclohexyl group include cyclohexyl, o-methylcyclohexyl, m-methylcyclohexyl, p-methylcyclohexyl, p-ethylcyclohexyl, p-propylcyclohexyl, p-isopropylcyclohexyl, p-butylcyclohexyl, p-tert-butylcyclohexyl, p-pentylcyclohexyl, p-hexylcyclohexyl, p-heptylcyclohexyl, p-octylcyclohexyl, p-nonylcyclohexyl, p-decylcyclohexyl, p-dodecylcyclohexyl, p-hexadecylcyclohexyl, p-acetylcyclohexyl, 3,4-dimethylcyclohexyl, 2,3-dimethylcyclohexyl, 2,6-dimethylcyclohexyl, 2,4,6-trimethylcyclohexyl, p-methoxycyclohexyl, p-ethoxycyclohexyl, p-butoxycyclohexyl, p-pentyloxycyclohexyl, p-hexyloxycyclohexyl, p-heptyloxycyclohexyl, p-octyloxycyclohexyl and p-nonyloxycyclohexyl.

The preferred compounds of formula (1) are as follows:
1. N-(cyclohexylidene)methylamine
2. N-(4-methylcyclohexylidene)methylamine
3. N-(4-methyloxycyclohexylidene)methylamine
4. N-(cyclohexylidene)aniline
5. N-(2-methylcyclohexylidene)aniline
6. N-(3-methylcyclohexylidene)aniline
7. N-(4-methylcyclohexylidene)aniline
8. N-(4-ethylcyclohexylidene)aniline
9. N-(2,6-dimethylcyclohexylidene)aniline 10. N-(4-methyloxycyclohexylidene)aniline
11. N-(4-fluorocyclohexylidene)aniline
12. N-(4-hydroxycyclohexylidene)aniline
13. N-(cyclohexylidene)-2-methylaniline
14. N-(2-methylcyclohexylidene)-2-methylaniline
15. N-(3-methylcyclohexylidene)-2-methylaniline
16. N-(4-methylcyclohexylidene)-2-methylaniline
17. N-(4-ethylcyclohexylidene)-2-methylaniline
18. N-(2,6-dimethylcyclohexylidene)-2-methylaniline
19. N-(4-methyloxycyclohexylidene)-2-methylaniline
20. N-(4-fluorocyclohexylidene)-2-methylaniline
21. N-(4-hydroxycyclohexylidene)-2-methylaniline
22. N-(cyclohexylidene)-3-methylaniline
23. N-(2-methylcyclohexylidene)-3-methylaniline
24. N-(3-methylcyclohexylidene)-3-methylaniline
25. N-(4-methylcyclohexylidene)-3-methylaniline
26. N-(4-ethylcyclohexylidene)-3-methylaniline
27. N-(2,6-dimethylcyclohexylidene)-3-methylaniline
28. N-(4-methyloxycyclohexylidene)-3-methylaniline
29. N-(4-fluorocyclohexylidene)-3-methylaniline
30. N-(4-hydroxycyclohexylidene)-3-methylaniline
31. N-(cyclohexylidene)-4-methylaniline
32. N-(2-methylcyclohexylidene)-4-methylaniline
33. N-(3-methylcyclohexylidene)-4-methylaniline
34. N-(4-methylcyclohexylidene)-4-methylaniline
35. N-(4-ethylcyclohexylidene)-4-methylaniline
36. N-(2,6-dimethylcyclohexylidene)-4-methylaniline
37. N-(4-methyloxycyclohexylidene)-4-methylaniline
38. N-(4-fluorocyclohexylidene)-4-methylaniline
39. N-(4-hydroxycyclohexylidene)-2-methylaniline
40. N-(cyclohexylidene)-2,4-dimethylaniline
41. N-(2-methylcyclohexylidene)-2,4-dimethylaniline
42. N-(3-methylcyclohexylidene)-2,4-dimethylaniline
43. N-(4-methylcyclohexylidene)-2,4-dimethylaniline
44. N-(4-ethylcyclohexylidene)-2,4-dimethylaniline
45. N-(2,6-dimethylcyclohexylidene)-2,4-(dimethylaniline)
46. N-(4-methyloxycyclohexylidene)-2,4-(dimethylaniline)
47. N-(4-fluorocyclohexylidene)-2,4-dimethylaniline
48. N-(4-hdyroxycyclohexylidene)-2,4-dimethylaniline
49. N-(cyclohexylidene)-4-methoxyaniline
50. N-(2-methylcyclohexylidene)-4-methoxyaniline
51. N-(3-methylcyclohexylidene)-4-methoxyaniline
52. N-(4-methylcyclohexylidene)-4-methoxyaniline
53. N-(4-ethylcyclohexylidene)-4-methoxyaniline
54. N-(2,6-dimethylcyclohexylidene)-4-methoxyaniline
55. N-(4-methyloxycyclohexylidene)-4-methoxyaniline
56. N-(4-fluorocyclohexylidene)-4-methoxyaniline
57. N-(4-hydroxycyclohexylidene)-4-methoxyaniline
58. N-(cyclohexylidene)-4-hydroxyaniline
59. N-(2-methylcyclohexylidene)-4-hydroxyaniline
60. N-(3-methylcyclohexylidene)-4-hydroxyaniline
61. N-(4-methylcyclohexylidene)-4-hydroxyaniline
62. N-(4-ethylcyclohexylidene)-4-hydroxyaniline
63. N-(2,6-dimethylcyclohexylidene)-4-hydroxyaniline
64. N-(4-methyloxycyclohexylidene)-4-hydroxyaniline
65. N-(4-fluorocyclohexylidene)-4-hydroxyaniline
66. N-(4-hydroxycyclohexylidene)-4-hydroxyaniline
67. N-(cyclohexylidene)benzylamine
68. N-(2-methylcyclohexylidene)benzylamine
69. N-(3-methylcyclohexylidene)benzylamine
70. N-(4-methylcyclohexylidene)benzylamine
71. N-(4-ethylcyclohexylidene)benzylamine
72. N-(2,6-dimethylcyclohexylidene)benzylamine
73. N-(4-methyloxycyclohexylidene)benzylamine
74. N-(4-fluorocyclohexyliene)benzylamine
75. N-(4-hydroxycyclohexylidene)benzylamine
76. N-(cyclohexylidene)cyclohexyl
77. N-(2-methylcyclohexylidene)cyclohexyl
78. N-(3-methylcyclohexylidene)cyclohexyl
79. N-(4-methylcyclohexylidene)cyclohexyl
80. N-(4-ethylcyclohexylidene)cyclohexyl
81. N-(2,6-dimethylcyclohexylidene)cyclohexyl
82. N-(4-methyloxycyclohexylidene)cyclohexyl
83. N-(4-fluorocyclohexylidene)cyclohexyl
84. N-(4-hydroxycyclohexylidene)cyclohexyl
85. N-(cyclohexylidene)-4-fluoroaniline
86. N-(2-methylcyclohexylidene)-4-fluoroaniline
87. N-(3-methylcyclohexylidene)-4-fluoroaniline
88. N-(4-methylcyclohexylidene)-4-fluoroaniline
89. N-(4-ethylcyclohexylidene)-4-fluroaniline
90. N-(2,6-dimethylcyclohexylidene)-4-fluroaniline
91. N-(4-methyloxycyclohexylidene)-4-fluoroaniline
92. N-(4-fluorocyclohexylidene)-4-fluoroaniline
93. N-(4-hydroxycyclohexylidene)-4-fluoroaniline
94. N-(2-methylcyclohexylidene)methylamine
95. N-(3-methylcyclohexylidene)methylamine
96. N-(4-ethylcyclohexylidene)methylamine
97. N-(2,6-dimethylcylohexylidene)methylamine
98. N-(4-methyloxycyclohexylidene)methylamine
99. N-(4-fluorocyclohexylidene)methylamine
100. N-(4-hydroxycyclohexylidene)methylamine
101. N-(cyclohexylidene)-4-phenoxyaniline
102. N-(2-methylcyclohexylidene)-4-phenoxyaniline
103. N-(3-methylcyclohexylidene)-4-phenoxyaniline
104. N-(4-methylcyclohexlidene)-4-phenoxyaniline
105. N-(4-ethylcyclohexylidene)-4-phenoxyaniline
106. N-(2,6-dimethylcyclohexylidene)-4-phenoxyaniline
107. N-(4-methyloxycyclohexylidene)-4-phenoxyaniline
108. N-(4-fluorocyclohexylidene)-4-phenoxyaniline
109. N-(4-hydroxycyclohexylidene)-4-phenoxyaniline
110. N-(cyclohexylidene)-4-fluoroaniline
111. N-(2-methylcyclohexylidene)-4-fluoroaniline
112. N-(3-methylcyclohexylidene)-4-fluroaniline
113. N-(4-methylcyclohexylidene)-4-fluroaniline
114. N-(4-ethylcyclohexylidene)-4-fluoroaniline
115. N-(2,6-dimethylcyclohexylidene)-4-fluoroaniline
116. N-(4-methyloxycyclohexylidene)-4-fluoroaniline
117. N-(4-fluorocyclohexylidene)-4-fluoroaniline
118. N-(4-hydroxycyclohexylidene)-4-fluoroaniline
119. N-(cyclohexylidene)-2-aminoaniline
120. N-(cyclohexylidene)-3-aminoaniline
121. N-(cyclohexylidene)-4-aminoaniline As the hydrogen moving catalyst, there can be used any known hydrogen moving catalyst. Typical examples of the hydrogen moving catalyst include Raney nickel, reduced nickel and nickel supporting catalysts obtained by supporting nickel on various carriers such as diatomaceous earth, alumina, pumice, silica gel and acidic terra abla; cobalt catalysts such as Raney cobalt, reduced cobalt, cobalt and cobalt-carrier catalysts; copper catalysts such as Raney copper, reduced copper and copper-carrier catalysts; palladium catalysts such as palladium black, palladium oxide, colloidal palladium, palladium-carbon, palladium-barium sulfate and palladium-barium carbonate; platinum catalysts such as platinum black, colloidal platinum, platinum sponge, platinum oxide, platinum sulfide, platinum-carbon and platinum-carrier catalysts; rhodium catalysts such as colloidal rhodium, rhodium-carbon and rhodium oxide; a platinum group catalyst such as a ruthenium catalyst; rhenium catalysts such as dirhenium heptaoxide and rhenium-carbon; a copper chromium oxide catalyst; a molybdenum oxide catalyst; a vanadium oxide catalyst; and a tungsten oxide catalyst. Among these catalysts, the palladium catalyst is preferable. In particular, the palladium-carrier catalyst is preferable. Above all, the palladium-carbon and palladium-alumina are most preferable.

The amount of the hydrogen moving catalyst is usually in the range of from 0.001 to 1.0 gram atom, preferably from 0.002 to 0.2 gram atom in terms of a metallic atom per gram molecule of the N-cyclohexylideneamino compound.

In the first aspect of the present invention, any of various reducing materials is used as a hydrogen acceptor. Examples of the hydrogen acceptor include olefin compounds such as 1-octene, allylbenzene and crotonic acid; nitro compounds such as 2,6-dimethylnitrobenzene, p-amylnitrobenzene, p-hexylnitrobenzene, p-octylnitrobenzene, p-sec-octylnitrobenzene, p-tert-octylnitrobenzene, p-nonylnitrobenzene, p-decylnitrobenzene, p-ethoxynitrobenzene, o-ethoxynitrobenzene, 2,6-dimethyl-4-aminonitrobenzene, nitrobenzene, p-dinitrobenzene, m-dinitrobenzene, 4-nitrodiphenyl, p-phenoxynitrobenzene, p-cyclohexylnitrobenzene, p-benzylnitrobenzene, nitromethane, 2-nitropropane, 1-nitronaphthalene, 2-, 3- and 4-nitrotoluenes, 4-nitroanisole, p-propylnitrobenzene, m-ethylnitrobenzene, 4-nitrobenzonitrile, p-nitroacetoanilide, 4-nitrobenzoic acid and nitrocyclohexane; phenols, for example, alkylphenols such as phenol, methylphenol, ethylphenol, isopropylphenol, butylphenol, 2,4-dimethylphenol, 2,4,6-trimethylphenol and 2,6-di-tert-butyl- 4-methylphenol as well as alkoxyphenols such as 3-methoxyphenol and 4-methoxyphenol.

However, in the case that the phenol is selected, it must be used in large quantities and there is the tendency that the amounts of by-products increase. It is particularly preferable to use nitrobenzene in the above-mentioned nitro compounds as the hydrogen acceptor, because nitrobenzene can be utilized as the material of N-cyclohexylideneaniline.

The amount of the hydrogen acceptor to be used depends upon its kind, but it is 5 equivalents of the hydrogen acceptor to the N-cyclohexylideneamino compound. Particularly in the case of the olefin or the nitro compound, the amount of the hydrogen acceptor is an equivalent or 50% excess of the N-cyclohexylideneamino compound. When the hydrogen acceptor is short, the by-product of N-cyclohexylamine tends to increase. As the hydrogen acceptor, the olefin or the nitro compound is preferable from the viewpoint of the volume efficiency of a reactor.

Examples of the sulfur-free polar solvent to be used include N,N-dimethylformamide, N,N-dimethylacetamide, tetramethylurea, methyl isobutyl ketone, tetrahydrofuran, dioxane, 1,3-dimethylimidazolizinone, glymes such as ethylene glycol dimethyl ether and diethylene glycol dimethyl ether, methyl salicylate, phenol and phenols, for example, alkylphenols such as methylphenol and 2,4,6-trimethylphenol as well as alkoxyphenols such as 3-methoxyphenol and 4-methoxyphenol. If necessary, they may be used in combinations of two or more thereof. Dimethyl sulfoxide and sulfolane are similarly within the category of the polar solvents, but they are not used because they contain sulfur which is poisonous to the dehydrogenation catalyst.

The amount of the sulfur-free polar solvent to be used is preferably 0.05–3.0 times by weight, more preferably 0.15–1.5 times by weight as much as that of the N-cyclohexylideneamino compound.

In placing the starting materials in a reactor, it is a preferable manner that the solvent and the catalyst are previously placed in the reactor and mixed, and the N-cyclohexylideneamino compound and the hydrogen acceptor are then simultaneously dropped into the reactor to carry out the above-mentioned reaction. Needless to say, alternatively, the N-cyclohexylideneamino compound and the hydrogen acceptor may be first mixed and then added into the reaction.

In the above-mentioned dehydrogenation reaction of the N-cyclohexylideneamino compound in the presence of the hydrogen moving catalyst and the hydrogen acceptor, an alkali metal compound and/or an alkaline earth metal compound can be added as a cocatalyst to the reaction system irrespective of the presence of the sulfur-free polar solvent. This is also one embodiment of the first aspect of the present invention.

Usable examples of the alkali metal compound and/or the alkaline earth metal compound which can be added as the cocatalyst are hydroxides, carbonates, bicarbonates and the like of alkali metals and alkaline earth metals. Typical examples of these compounds include lithium hydroxide, sodium hydroxide, potassium hydroxide, calcium hydroxide, magnesium hydroxide, sodium carbonate, potassium carbonate and sodium hydrogen carbonate. Above all, sodium hydroxide and potassium hydroxide are preferable. These cocatalysts may be used singly or in combination of two or more thereof. The cocatalyst does not have to be added to the reaction system separately from the above-mentioned dehydrogenation catalyst. For example, after a noble metal supporting catalyst has been prepared, a salt, a hydroxide or the like of an alkali metal and/or an alkaline earth metal may be additionally supported as the alkali metal component and/or the alkaline earth metal component on the noble metal supporting catalyst, and the thus formed catalyst may be used.

The amount of the cocatalyst is preferably in the range of from 2 to 30% by weight, more preferably from 5 to 20% by weight, in terms of the alkali metal and/or the alkaline earth metal, based on the weight of the catalyst metal. If the amount of the cocatalyst is in excess of this range, a reaction rate tends to deteriorate, and conversely if it is less than the range, the yield is low.

It is advantageous that the reaction is carried out under the removal of water, and thus a technique is suitable in which water is removed from the reaction mixture while azeotropic distillation is done by the use of a solvent such as benzene, toluene or xylene.

The temperature of the reaction is usually in the range of from 120° to 250° C., preferably from 140° to 200° C.

The mixture obtained by the above-mentioned method is treated in an ordinary manner such as distillation, crystallization or extraction. For example, the solution in which the reaction has already been brought to an end is filtered to separate the catalyst therefrom. The thus recovered catalyst can be reused. The resultant filtrate is concentrated to recover the solvent. The produced aromatic secondary amino compound in the reactor can be directly used without any treatment, but if necessary, it may be purified by distillation, crystallization or the like.

The second aspect of the present invention is directed to a method for preparing an aromatic secondary amino compound represented by the formula (2)

(2)

wherein each R is a hydrogen atom, alkyl group, alkoxy group, amino group, hydroxyl group or fluorine; R' is an alkyl group, phenyl group, benzyl group, naphthyl group, furyl group, furfuryl group or cyclohexyl group, and R' may be substituted by an alkyl group, alkoxy group, phenyl group, phenoxy group, cyclohexyl group, amino group, substituted amino group, carboxyl group, hydroxyl group or fluorine; and n is an integer of from 0 to 5 which comprises the step of reacting cyclohexanone or a nucleus-substituted cyclohexanone represented by the formula (3)

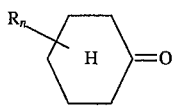
(3)

wherein R is defined above, an amine represented by the formula (4)

R'—NH$_2$ (4)

wherein R' is defined above, and a nitro compound corresponding to the amine and represented by the formula (5)

R'—NO$_2$ (5)

wherein R' is defined above as a hydrogen acceptor in a sulfur-free polar solvent in the presence of a hydrogen moving catalyst.

That is, the second aspect of the present invention is directed to a method for preparing an aromatic secondary amino compound which is characterized by comprising the step of reacting cyclohexanone or a nucleus-substituted cyclohexanone, an amine and a nitro compound as a hydrogen acceptor corresponding to the amine in a sulfur-free polar solvent in the presence of a hydrogen moving catalyst.

Examples of the alkyl group represented by R' in the formulae (4) and (5) include methyl, ethyl, propyl, isopropyl, butyl, isobutyl, tert-butyl, aminomethyl, aminoethyl, aminopropyl, 2-aminopropyl, 3-aminopropyl, aminobutyl and hydoxyethyl.

Examples of the phenyl group include phenyl, o-methylphenyl, m-methylphenyl, p-methylphenyl, p-ethyl-phenyl, p-propylphenyl, p-isopropylphenyl, p-butylphenyl, p-tert-butylphenyl, p-pentylphenyl, p-hexylphenyl, p-heptylphenyl, p-octylphenyl, p-nonylphenyl, p-decylphenyl, p-dodecylphenyl, p-hexadecylphenyl, 3,4-dimethylphenyl, 2,3-dimethylphenyl, 2,6-dimethylphenyl, 2,4,6-trimethylphenyl, p-methoxyphenyl, p-ethoxyphenyl, p-butoxyphenyl, p-pentyloxyphenyl, p-hexyloxyphenyl, p-heptyloxyphenyl, p-octyloxyphenyl, p-nonyloxyphenyl, p-phenyloxyphenyl, p-trioxyphenyl, p-acetylphenyl, p-benzoylphenyl, o-aminophenyl, m-aminophenyl, p-aminophenyl, p-methylaminophenyl, p-ethylaminophenyl, p-butylaminophenyl, p-tert-butylaminophenyl, p-octylaminophenyl, p-dodecylaminophenyl, p-cyclohexylphenyl, p-methylcyclohexylphenyl, p-ethylcyclohexylphenyl, p-propylcyclohexylphenyl, p-hydroxyphenyl, p-carboxyphenyl and p-fluorophenyl, and phenyl and p-methylphenyl are preferable.

Examples of the benzyl group include benzyl, o-methylbenzyl, m-methylbenzyl, p-methylbenzyl, p-ethylbenzyl, p-propylbenzyl, p-isopropylbenzyl, p-butylbenzyl, p-tert-butylbenzyl, p-pentylbenzyl, p-hexylbenzyl, p-heptylbenzyl, p-octylbenzyl, p-nonylbenzyl, p-decylbenzyl, p-dodecylbenzyl, p-hexadecylbenzyl, p-acetylbenzyl, 3,4-dimethylbenzyl, 2,3-dimethylbenzyl, 2,6-dimethylbenzyl, 2,4,6-trimethylbenzyl, p-methoxybenzyl, p-ethoxybenzyl, p-butoxybenzyl, p-pentyloxybenzyl, p-hexyloxybenzyl, p-heptyloxybenzyl, p-octyloxybenzyl, p-nonyloxybenzyl, p-phenyloxybenzyl, p-tolyloxybenzyl, p-benzoylbenzyl, p-methylaminobenzyl, p-ethylaminobenzyl, p-butylaminobenzyl, p-tert-butylaminobenzyl, p-octylaminobenzyl, p-dodecylaminobenzyl, p-cyclohexylbenzyl, p-methylcyclo-hexylbenzyl, p-ethylcyclohexylbenzyl, p-propylcyclo-hexyl-benzyl, p-hydroxybenzyl, p-carboxybenzyl and p-fluorobenzyl.

Examples of the cyclohexyl group include cyclohexyl, o-methylcyclohexyl, m-methylcyclohexyl, p-methylcyclohexyl, p-ethylcyclohexyl, p-propylcyclohexyl, p-isopropylcyclohexyl, p-butylcyclohexyl, p-tert-butylcyclohexyl, p-pentylcyclohexyl, p-hexylcyclohexyl, p-heptylcyclohexyl, p-octylcyclohexyl, p-nonylcyclohexyl, p-decylcyclohexyl, p-dodecylcyclohexyl, p-hexadecylcyclohexyl, p-acetylcyclohexyl, 3,4-dimethylcyclohexyl, 2,3-dimethylcyclohexyl, 2,6-dimethylcyclohexyl, 2,4,6-trimethylcyclohexyl, p-methoxycyclohexyl, p-ethoxycyclohexyl, p-butoxycyclohexyl, p-pentyloxycyclohexyl, p-hexyloxycyclohexyl, p-heptyloxycyclohexyl, p-octyloxycyclohexyl and p-nonyloxycyclohexyl.

The preferred compounds of formula (3) are as follows:
1. cyclohexanone
2. 2-methylcyclohexanone
3. 3-methylcyclohexanone
4. 4-methylcyclohexanone
5. 4-ethylcyclohexanone
6. 4-octylcyclohexanone
7. 2,6-dimethylcyclohexanone
8. 2,4-dimethylcyclohexanone
9. 4-phenylcyclohexanone
10. 4-phenylmethylcyclohexanone
11. 4-phenyloxycyclohexanone
12. 4-methyloxycyclohexanone
13. 4-nonyloxycyclohexanone
14. 4-methylaminocyclohexanone
15. 4-dimethylaminocyclohexanone
16. 4-acetylaminocyclohexanone
17. 4-fluorocyclohexanone
18. 4-hydroxycyclohexanone The preferred compounds of formula (4) are as follows:
1. methylamine
2. ethylamine
3. aniline
4. 2-methylaniline
5. 3-methylaniline
6. 4-methylaniline
7. 4-ethylaniline
8. 4-nonylaniline
9. 2,6-dimethylaniline
10. 2,4-dimethylaniline
11. 2,4,6-trimethylaniline
12. 4-methoxyaniline
13. 2-methyl-4-methoxyaniline
14. 4-acetylaniline
15. 4-aminoacetoanilide
16. 4-methylaminoaniline
17. 4-cyclohexylaniline
18. 4-hydroxyaniline
19. 4-carboxyaniline
20. benzylamine
21. 4-methylbenzylamine
22. 4-octylbenzylamine
23. 2,4-dimethylbenzylamine
24. 4-methoxybenzylanline
25. cyclohexylamine
26. 4-methylcyclohexylamine
27. 4-methyloxycycloamine
28. 2-naphthylamine
29. furfurylamine
30. 4-fluoroaniline
31. 4-aminodiphenylether
32. orthophenylenediamine 33. metaphenylenediamine
34. paraphenylenediamine The preferred compounds of formula (5) are as follows:
1. nitromethane
2. nitroethane
3. nitrobenzene
4. 2-nitrotoluene
5. 3-nitrotoluene
6. 4-nitrotoluene
7. 4-ethylnitrobenzene
8. 4-nonylnitrobenzene
9. 2,6-dimethylnitrobenzene
10. 2,4-dimethylnitrobenzene
11. 2,4,6-trimethylnitrobezene
12. 4-methyoxynitrobenzene
13. 2-methyl-4-methoxynitrobenzene
14. 4-acetylnitrobezene
15. 4-nitroacetoanilide
16. 4-methylaminonitrobenzene
17. 4-cyclohexylnitrobenzene
18. 4-hydroxynitrobenzene
19. 4-carboxynitrobenzene
20. nitrobenzyl
21. 4-methylnitrobenzyl
22. 4-octylnitrobenzyl
23. 2,4-dimethylnitrobenzyl
24. 4-methoxynitrobenzyl
25. nitrocyclohexanone
26. 4-methylnitrocyclohexanone
27. 4-methoxynitrocyclohexanone
28. 2-nitronaphthalene
29. nitrofurfuryl
30. 4-fluoronitrobenzene
31. 4-nitrodiphenylether
32. orthonitroaniline
33. metanitroaniline
34. paranitroaniline In the present invention, a molar ratio of the cyclohexanone or the nucleus-substituted cyclohexanone represented by the formula (3):the amine represented by the formula (4):the nitro compound represented by the formula (5) is usually 3:1:2, and this ratio can be suitably altered on the basis of the given values. The nitro compound behaves as the hydrogen acceptor to produce the amine in the reaction system, and this amine causes a condensation reaction with the cyclohexanone or the nucleus-substituted cyclohexanone which is another starting material, to produce a Schiff base. Afterward, the Schiff base is subjected to dehydrogenation, thereby producing an aromatic secondary amino compound. In the dehydrogenation of the Schiff base, hydrogen is generated, and $\frac{2}{3}$ mol of the nitro compound per mol of the Schiff base can be converted into the amine by the thus generated hydrogen.

Therefore, in order to completely effectively utilize the hydrogen generated in the system, it is necessary to react the cyclohexanone or the nucleus-substituted cyclohexanone and the nitro compound in a molar ratio of 3:2. In this case, however, the excessive amount of the cyclohexanone or the nucleus-substituted cyclohexanone further reacts with the aromatic secondary amino compound produced in the system, so that an aromatic tertiary amino compound tends to be produced as a by-product. Conversely, if the amount of the nitro compound is excessive, the reaction rate tends to deteriorate inconveniently. For the purpose of avoiding these drawbacks, it is preferable that a molar ratio of the cyclohexanone or the nucleus-substituted cyclohexanone:the amine compound:the nitro compound is 3:1:2, and more preferably, a molar ratio of the sum of the nitro compound and the amine compound to the cyclohexanone or the nucleus-substituted cyclohexanone is in the range of from 0.9 to 1.2.

As the hydrogen moving catalyst which can be used in the method of the present invention, there can be used any known hydrogen moving catalyst. Typical examples of the hydrogen moving catalyst include Raney nickel, reduced nickel and nickel supporting catalysts obtained by supporting nickel on various carriers such as diatomaceous earth, alumina, pumice, silica gel and acidic terra abla; cobalt catalysts such as Raney cobalt, reduced cobalt, cobalt and cobalt-carrier catalysts; copper catalysts such as Raney copper, reduced copper and copper-carrier catalysts; palladium catalysts such as palladium black, palladium oxide, colloidal palladium, palladium-carbon, palladium-barium sulfate and palladium-barium carbonate; platinum catalysts such as platinum black, colloidal platinum, platinum sponge, platinum oxide, platinum sulfide, and platinum-carrier catalysts such as platinum-carbon; rhodium catalysts such as colloidal rhodium, rhodium-carbon and rhodium oxide; a platinum group catalyst such as a ruthenium catalyst; rhenium catalysts such as dirhenium heptaoxide and rhenium-carbon; a copper chromium oxide catalyst; a molybdenum oxide catalyst; a vanadium oxide catalyst; and a tungsten oxide catalyst. Among these catalysts, the palladium catalyst is preferable. In particular, the palladium-carrier catalyst is preferable. Above all, the palladium-carbon and palladium-alumina are most preferable.

The amount of the hydrogen moving catalyst to be used is usually in the range of from 0.001 to 1.0 gram atom, preferably from 0.002 to 0.2 gram atom in terms of a metallic atom per gram molecule of the amine.

The method of the present invention is characterized by using a sulfur-free polar solvent. Examples of the sulfur-free polar solvent include N,N-dimethylformamide, N,N-dimethylacetamide, tetramethylurea, methyl isobutyl ketone, tetrahydrofuran, dioxane, 1,3-dimethylimidazolizinone, glymes such as ethylene glycol dimethyl ether and diethylene glycol dimethyl ether, methyl salicylate, phenol and phenols, for example, alkylphenols such as methylphenol and 2,4,6-trimethylphenol as well as alkoxyphenols such as 3-methoxyphenol and 4-methoxyphenol. If necessary, they may be used in combinations of two or more thereof. Dimethyl sulfoxide and sulfolane are similarly within the category of the polar solvents, but they are not used because they contain sulfur which is poisonous to the hydrogen moving catalyst.

The amount of the sulfur-free polar solvent to be used is preferably 0.1–6.0 times by weight, more preferably 0.3–3.0 times by weight of the cyclohexanone or the nucleus-substituted cyclohexanone.

It is also within the category of the present invention to use an alkaline metal compound and/or an alkaline earth metal compound as a cocatalyst. The use of the cocatalyst leads to the effect that the life of the hydrogen moving catalyst can be prolonged.

Usable examples of the alkali metal compound and/or the alkaline earth metal compound which can be added as the cocatalyst are hydroxides, carbonates, bicarbonates and the like of alkali metals and alkaline earth metals. Typical examples of these compounds include lithium hydroxide, sodium hydroxide, potassium hydroxide, calcium hydroxide, magnesium hydroxide, sodium carbonate, potassium carbonate and sodium hydrogen carbonate. Above all, sodium hydroxide and potassium hydroxide are preferable. These cocatalysts may be used singly or in combinations of two or more thereof. The cocatalyst does not have to be added to the reaction system separately from the above-mentioned dehydrogenation catalyst. For example, after a noble metal supporting catalyst has been prepared, a salt, a hydroxide or the like of an alkali metal and/or an alkaline earth metal may be additionally supported as the alkali metal component and/or the alkaline earth metal component on the noble metal supporting catalyst, and the thus formed catalyst may be used.

The amount of the cocatalyst to be used is preferably in the range of from 2 to 30% by weight, more preferably from 5 to 20% by weight, in terms of the alkali metal and/or the alkaline earth metal, based on the weight of the catalyst metal.

It is also a preferable embodiment of the present invention to add, to the reaction using the above-mentioned cocatalyst, an organic acid in which a logarithm (pKa) of a reciprocal of an acid dissociation constant is in the range of from 3.5 to 6.0.

The preferable pKa of the organic acid is in the range of from 4.0 to 5.0. If the pKa of the organic acid is less than this range, the Schiff base is unstable, and if it is more than the above-mentioned range, the dehydrogenation reaction is impaired. Examples of the organic acid include acetic acid, propionic acid, butyric acid, isobutyric acid, valerianic acid, isovalerianic acid, hexanic acid, cyclohexanecarboxylic acid, octanoic acid, crotonic acid, vinylacetic acid, benzoic acid, anisic acid, cinnamic acid, phenylacetic acid and 2-naphthoic acid. The amount of the organic acid to be used is preferably in the range of from 50 to 2000% by weight, more preferably from 70 to 800% by weight based on the weight of the catalyst metal.

In the case that the nitro compound is used as the hydrogen acceptor in the presence of the catalyst of a noble metal in the group VIII and the sulfur-free solvent to produce the amine and the cyclohexanone or the nucleus-substituted cyclohexanone is simultaneously reacted with the amine to prepare the aromatic secondary amino compound, the used catalyst can be recovered and then reused. In this case, if the alkali metal compound and/or the alkaline earth metal compound as the cocatalyst and the organic acid having a pKa of 3.5 to 6.0 are added to the reaction system, the amount of the catalyst to be added in each operation can be decreased as much as possible, and a reaction rate and a yield can be maintained.

It is advantageous that the reaction is carried out under the removal of water, and thus a technique is suitable in which water is removed from the reaction mixture while azeotropic distillation is done by the use of a solvent such as benzene, toluene or xylene.

The temperature at the reaction is usually in the range of from 120° to 250° C., preferably from 140° to 200° C.

In the above-mentioned reaction, when the raw materials are placed in a reactor, it is a preferable manner that the (co)catalyst, the solvent and the amine are previously put in the reactor, stirred and then heated, and the (nucleus-substituted) cyclohexanone and the nitro compound are then simultaneously dropped into the reactor to carry out the above-mentioned reaction. Needless to say, the (nucleus-substituted) cyclohexanone and the nitro compound are first mixed and then added to the reaction.

The mixture obtained by the above-mentioned reaction is treated in an ordinary manner such as distillation, crystallization or extraction. For example, the solution in which the reaction has already been brought to an end is filtered to separate the catalyst therefrom. The thus recovered catalyst can be reused. The resultant filtrate can be concentrated to recover the solvent. The produced aromatic secondary amino compound in the reactor can be directly used without any treatment, but if necessary, it may be purified by distillation, crystallization or the like.

In accordance with the further aspect of the invention wherein aminodiphenylamine (hereinafter abbreviated as "ADPA") is prepared by reacting phenylenediamine (hereinafter abbreviated as "PD") with cyclohexanone in the presence of a hydrogen transfer catalyst in a sulfur-free polar solvent while using nitroaniline (hereinafter abbreviated as "NA") as a hydrogen acceptor, it is important to use a sulfur-free polar solvent. Examples of the sulfur-free polar solvent include N,N-dimethylformamide, N,N-dimethylacetamide; tetramethylurea; methyl isobutyl ketone, tetrahydrofuran, dioxane and 1,3-dimethylimidazolidinone; glymes such as ethylene glycol dimethyl ether, diethylene glycol dimethyl ether and triethylene glycol dimethyl ether; and phenols such as methyl salicylate, phenol, alkylphenols such as methylphenol and 2,4,6-trimethylphenol, and alkoxyphenols such as 3-methoxyphenol and 4-methoxyphenol. These solvents can be used either singly or in combination.

Incidentally, sulfur-containing polar solvents such as dimethylsulfoxide and sulfolane exhibit poisonous action against hydrogen transfer catalysts and are hence not preferred.

Any known hydrogen transfer (moving) catalysts can be used in the process of the present invention. Specific examples include those mentioned above including nickel/ carrier catalysts such as those formed by having Raney nickel, reduced nickel or nickel borne on various carriers such as diatomaceous earth, alumina, pumice, silica gel and acid clay; cobalt catalysts such as Raney cobalt, reduced cobalt, cobalt and cobalt/carrier catalysts; palladium catalysts such as palladium black, palladium oxide, colloidal palladium, palladium/carbon, palladium/barium sulfate and palladium/barium carbonate; platinum catalysts such as platinum black, colloidal platinum, platinized sponge, platinum oxide, platinum sulfide and platinum/carbon; rhodium catalysts such as colloidal rhodium, rhodium/carbon and rhodium oxide; platinum group catalysts such as ruthenium catalysts; rhenium catalysts such as dirhenium heptaoxide and rhenium/carbon; copper chromate catalysts; molybdenum oxide catalysts; vanadium oxide catalysts; and tungsten oxide catalysts. Among these catalysts, it is preferred to use a palladium catalyst. In particular, use of a palladium/carrier catalyst, notably a palladium/carbon or palladium/alumina is preferred. These hydrogen transfer catalysts can be used generally in a proportion of 0.001–1.0 gram atom, preferably 0.002–0.2 gram atom in terms of metal atoms per gram molecule of cyclohexanone.

According to the method of the further aspect of the present invention, a Schiff base is formed by condensation of PD and cyclohexanone, followed by the formation of ADPA through dehydrogenation. During the method, NA is used as a receptor for resulting hydrogen. In this manner, NA is converted to PD in the reaction system and by the reaction of the PD and the other raw material, that is, cyclohexanone, ADPA is formed further.

At this time, it is possible to convert 0.67 mole of NA to PD per mole of the Schiff base. For the full and effective utilization of hydrogen occurring in the reaction system, it is therefore sufficient if the molar ratio of NA to cyclohexanone is set at 0.67. Abundance of NA at this stage tends to result in a lower reaction velocity and is hence not beneficial. An unduly small molar ratio of PD/cyclohexanone, on the other hand, tends to cause further reaction of ADPA, which has been formed in the reaction system, with cyclohexanone so that N,N'-diphenylphenylene-diamine (hereinafter abbreviated as "N,N'-DPPA") would be by-produced. To avoid these drawbacks, it is preferred to add 0.67 mole of NA and at least 0.33 mole of PD per mole of cyclohexanone from the beginning of the reaction and then to react them. It is more preferred to conduct the reaction with the sum of NA and PD being maintained at 1.4 moles or more, especially 1.7 mole or more per mole of cyclohexanone.

In the method of this aspect of the present invention, all the raw materials can be charged together at once in a reaction vessel at the beginning of the reaction. It is however important to conduct the reaction while simultaneously adding cyclohexanone and NA dropwise into a liquid mixture of the hydrogen transfer catalyst, PD and the sulfur-free polar solvent. Needless to say, they can be mixed first and then added dropwise. This makes it possible to always maintain the PD/cyclohexanone molar ratio at a still higher level in the reaction system, thereby allowing the target product to be obtained in a high yield.

The reaction can also be conducted while separating water from the reaction mixture by azeotropically distilling it off together with a solvent such as benzene, toluene or xylene.

The reaction temperature can be selected generally from a range of 140°–250° C., preferably from a range of 160°–200° C.

The ADPA so formed can be obtained by processing the reaction mixture in a manner known per se in the art, such as distillation, crystallization or extraction, after the completion of the reaction. For example, the reaction mixture is filtered subsequent to the completion of the reaction, whereby the catalyst is separated. The catalyst so recovered can be reused. The filtrate is concentrated to recover the solvent. The ADPA left in the reaction vessel can be used, as is, as a raw material for the next reaction in some instances but, if necessary, is purified by distillation, crystallization or the like.

According to the present invention, the desired aromatic secondary amino compound can be obtained under extremely moderate conditions and in a high yield.

Now, the various aspects of the present invention will be described in detail in reference to examples.

EXAMPLE A1

In a 100 ml round bottom flask equipped with a reflux condenser with a separator, a thermometer and a stirrer were placed 1.6 g of 5% Pd/C containing 50% of water made by N.E. Chemcat Co., Ltd., 10 g of diethylene glycol dimethyl ether, 17.33 g (0.1 mol) of N-cyclohexylidene aniline and 8.29 g (0.067 mol) of nitrobenzene. Afterward, the reactor was heated up to 160° C. with stirring, and reaction was then carried out for 4 hours by maintaining the reactor at 158°–162° C. During this reaction, water present in the catalyst and water produced by the reaction were removed from the reaction system by adding benzene to the reactor to cause azeotropy, condensing water by the reflux condenser, and then separating it by the separator. The amount of the removed water was 1.8 g. Next, the reaction solution was cooled to room temperature, and the 5% Pd/C was then removed from the reaction solution by filtration. The resultant filtrate was analyzed by the use of gas chromatography. The conversion of an imine was 100%, and the yield of diphenylamine was 87.6%.

EXAMPLES A2 TO A8

Reactions were carried out by the same procedure as in Example A1 except that diethylene glycol dimethyl ether in Example A1 was replaced with various polar solvents shown in Table 1.

The results are set forth in Table 1.

TABLE 1

| Example | Solvent | Conversion of Imine (mol %) | Yield of Diphenylamine (mol %) |
|---|---|---|---|
| A2 | N,N-dimethylacetamide | 100.0 | 89.5 |
| A3 | N,N'-dimethylimidazolidinone | 100.0 | 88.2 |
| A4 | p-cresol | 99.3 | 84.1 |
| A5 | N,N-dimethylformamide | 100.0 | 87.7 |
| A6 | Tetramethylurea | 99.5 | 87.0 |
| A7 | N-methylpyrrolidone | 98.9 | 83.8 |
| A8 | Methyl salicylate | 99.8 | 86.5 |

EXAMPLE A9

Reaction was carried out by the same procedure as in Example A1 except that in place of nitrobenzene in Example A1, 23.87 g (0.202 mol) of a-methylstyrene were used as a hydrogen acceptor. As a result, the conversion of an imine was 100%, and the yield of diphenylamine was 85.9%.

COMPARATIVE EXAMPLE A1

Reaction was carried out by the same procedure as in Example A1 except that diethylene glycol dimethyl ether was not used. As a result, the conversion of an imine was 96.1%, and the yield of diphenylamine was 72.3%.

COMPARATIVE EXAMPLE A2

Reaction was carried out by the same procedure as in Example A1 except that in place of diethylene glycol dimethyl ether in Example A1, p-tert-butyltoluene was used as a solvent. As a result, the conversion of an imine was 94.0%, and the yield of diphenylamine was 72.6%.

EXAMPLE B1

In a 100 ml round bottom flask equipped with a reflux condenser with a separator, a thermometer and a stirrer were placed 2.57 g of 5% Pd/C containing 50% of water made by N.E. Chemcat Co., Ltd., 22.23 g of N,N-dimethylformamide, 20–51 g (0.1 mol) of N-(4-methylcyclohexylidene)-4-methylaniline and 9.24 g (0.067 mol) of p-nitrotoluene. Afterward, the reactor was heated up to 140° C. with stirring, and reaction was then carried out for 4 hours by maintaining the reactor at 138°–142° C. During this reaction, water present in the catalyst and water produced by the reaction were removed from the reaction system by adding benzene to the reactor to cause azeotropy, condensing water by the reflux condenser, and then separating it by the separator. The amount of the removed water was 2.9 g. Next, the reaction solution was cooled to room temperature, and the 5% Pd/C was then removed from the reaction solution by filtration. The resultant filtrate was analyzed by the use of gas chromatography. The conversion of an imine was 100%, and the yield of 4,4'-dimethyldiphenylamine was 85.3%.

EXAMPLES B2 TO B6

Reactions were carried out by the same procedure as in Example B1 except that N,N-dimethylformamide in Example B1 was replaced with various polar solvents shown in Table 2 and reaction temperature was set to 160° C. The results are set forth in Table 2.

TABLE 2

| Example | Solvent | Conversion of Imine (mol %) | Yield of Diphenylamine (mol %) |
|---|---|---|---|
| B2 | N,N'-dimethylimidazolidinine | 99.4 | 94.9 |
| B3 | p-cresol | 99.6 | 91.4 |
| B4 | Phenol | 99.5 | 88.3 |
| B5 | Diethylene glycol dimethyl ether | 99.5 | 91.1 |
| B6 | p-methoxyphenol | 99.8 | 93.4 |

EXAMPLES B7 TO B14

Reactions were carried out by the same procedure as in Example B1 except that in place of the combination of N-(4-methylcyclohexylidene)-4-methylaniline and p-nitrotoluene in Example B1, combinations of various N-cyclohexylidene amino compounds and hydrogen acceptors shown in Table 3 were used.

The results are set forth in Table 3.

TABLE 3

| Example | N-Cyclohexylidene-amino Compound | Hydrogen Acceptor | Conversion (mol %) | Yield (mol %) |
|---|---|---|---|---|
| B7 | N-(4-methylcyclohexylidene)-2-methylaniline | o-nitrotoluene | 96.2 | 90.8 |
| B8 | N-(3-ethylcyclohexylidene)-4-methylaniline | p-nitrotoluene | 99.1 | 94.2 |
| B9 | N-(2-methylcyclohexylidene)-4-methylaniline | p-nitrotoluene | 100.0 | 96.1 |
| B10 | N-cyclohexylidene-3-ethylaniline | m-nitrotoluene | 98.9 | 92.1 |
| B11 | N-(4-methylcyclohexylidene)-4-methoxyaniline | 4-nitroanisole | 99.2 | 93.1 |
| B12 | N-(4-methylcyclohexylidene)-4-phenoxyaniline | 4-nitrodiphenylether | 99.3 | 93.2 |
| B13 | N-(4-methoxycyclohexylidene)-4-fluoroaniline | 4-fluoronitrobenzene | 92.3 | 89.1 |
| B14 | N-(4-methylcyclohexylidene)-4-hydroxyaniline | 4-nitrophenol | 95.6 | 91.1 |

EXAMPLE B15

Reaction was carried out by the same procedure as in Example B1 except that in place of p-nitrotoluene in Example B1, 23.87 g (0.202 mol) of α-methylstyrene were used as a hydrogen acceptor. As a result, the conversion of an imine was 89.1%, and the yield of 4,4'-dimethyldiphenylamine was 82.1%.

COMPARATIVE EXAMPLE B1

Reaction was carried out by the same procedure as in Example B1 except that N,N-dimethylformamide was not used. As a result, the conversion of an imine was 51.9%, and the yield of 4,4'-dimethyldiphenylamine was 37.4%.

COMPARATIVE EXAMPLE B2

Reaction was carried out by the same procedure as in Example B1 except that in place of N,N-dimethylformamide in Example B1, p-tert-butyltoluene was used as a solvent. As a result, the conversion of an imine was 49.1%, and the yield of 4,4'-dimethyldiphenylamine was 35.3%.

COMPARATIVE EXAMPLE B3

Reaction was carried out by the same procedure as in Example B7 except that N,N-dimethylformamide was not used. As a result, the conversion of an imine was 31.3%, and the yield of 4,2'-dimethyldiphenylamine was 15.5%.

COMPARATIVE EXAMPLE B4

Reaction was carried out by the same procedure as in Example B9 except that N,N-dimethylformamide was not used. As a result, the conversion of an imine was 12.1%, and the yield of 2,4'-dimethyldiphenylamine was 4.3%.

EXAMPLE C1

In a 200 ml round bottom flask equipped with a reflux condenser with a separator, a thermometer, a dropping device and a stirrer were placed 3.72 g of 5% Pd/C containing 50% of water made by N.E. Chemcat Co., Ltd. and 20 g of diethylene glycol dimethyl ether, and in the dropping device was prepared a mixed solution of 34.66 g (0.2 mol) of N-cyclohexylidene aniline and 16.58 g (0.13 mol) of nitrobenzene. Afterward, the reactor was heated up to 160° C. with stirring, and after the removal of water present in the catalyst, the solution in the dropping device was dropped over 4 hours, while a temperature of 158°–162° C. was maintained. After completion of the dropping, the solution was stirred for 0.5 hour, while this temperature range was maintained. Water produced during this step was removed from the reaction system by adding benzene to the reactor to cause azeotropy, condensing water by the reflux condenser, and then separating it by the separator. The amount of the removed water was 4.8 g. Next, the reaction solution in the reactor was cooled to room temperature, and the 5% Pd/C was then removed from the reaction solution by filtration. The resultant filtrate was analyzed by the use of gas chromatography. The conversion of an imine was 100%, and the yield of diphenylamine was 98.5%.

EXAMPLES C2 TO C8

Reactions were carried out by the same procedure as in Example C1 except that diethylene glycol dimethyl ether in Example C1 was replaced with various polar solvents shown in Table 4.

The results are set forth in Table 4.

COMPARATIVE EXAMPLE C1

Reaction was carried out by the same procedure as in Example C1 except that in place of diethylene glycol dimethyl ether in Example C1, p-tert-butyltoluene was used as a solvent. As a result, the conversion of an imine was 35.0%, and the selectivity of diphenylamine was 90.2%.

TABLE 4

| Example | Solvent | Conversion of Imine (mol %) | Yield of Diphenylamine (mol %) |
|---|---|---|---|
| C2 | Diethylene glycol diethyl ether | 100.0 | 98.4 |
| C3 | N,N'-dimethylimidazolidinone | 100.0 | 98.5 |
| C4 | N,N- | 100.0 | 98.7 |

TABLE 4-continued

| Example | Solvent | Conversion of Imine (mol %) | Yield of Diphenylamine (mol %) |
|---------|---------|-----------------------------|-------------------------------|
| C5 | dimethylformamide N,N-dimethylacetamide | 100.0 | 99.0 |
| C6 | Tetramethylurea | 99.0 | 97.0 |
| C7 | N-methylpyrrolidone | 91.0 | 89.3 |
| C8 | Methyl salicylate | 97.0 | 95.0 |
| C9 | p-cresol | 98.0 | 96.5 |

EXAMPLE D1

In a 100 ml round bottom flask equipped with a reflux condenser with a separator, a thermometer and a stirrer were placed 2.57 g of 5% Pd/C containing 50% of water made by N.E. Chemcat Co., Ltd. and 22.23 g of N,N-dimethylformamide, and in the dropping device was prepared and stored a mixed solution of 20.51 g (0.1 mol) of N-(4-methylcyclohexylidene)-4-methylaniline and 9.24 g (0.067 mol) of p-nitrotoluene. Afterward, the reactor was heated up to 140° C. with stirring, and after the removal of water present in the catalyst, the solution in the dropping device was dropped over 4 hours, while a temperature of 138°–142° C. was maintained. After completion of the dropping, the solution was stirred for 1 hour, while this temperature range was maintained. Water produced during this step was removed from the reaction system by adding benzene to the reactor to cause azeotropy, condensing water by the reflux condenser, and then separating it by the separator. The amount of the removed water was 4.0 g. Next, the reaction solution was cooled to room temperature, and the 5% Pd/C was then removed from the reaction solution by filtration. The resultant filtrate was analyzed by the use of gas chromatography. The conversion of an imine was 98.6%, and the yield of 4,4'-dimethyldiphenylamine was 93.5%.

EXAMPLES D2 TO D6

Reactions were carried out by the same procedure as in Example D1 except that N,N-dimethylformamide in Example D1 was replaced with various polar solvents shown in Table 5 and reaction temperature was set to 160° C.

The results are set forth in Table 5.

TABLE 5

| Example | Solvent | Conversion of Imine (mol %) | Yield of Ditolylamine (mol %) |
|---------|---------|-----------------------------|-------------------------------|
| D2 | N,N'-dimethylimidazolidinone | 98.2 | 96.3 |
| D3 | p-cresol | 99.1 | 94.1 |
| D4 | Phenol | 99.0 | 93.4 |
| D5 | Diethylene glycol dimethyl ether | 98.3 | 95.2 |
| D6 | p-methoxyphenol | 99.2 | 95.3 |

EXAMPLES D7 TO D14

Reactions were carried out by the same procedure as in Example D1 except that the combination of N-cyclohexylidene amino compound and a hydrogen acceptor in Example D1 was changed to combinations shown in Table 6.

The results are set forth in Table 6.

TABLE 6

| Example | N-Cyclohexylidene-amino Compound | Hydrogen Acceptor | Conversion (mol %) | Yield (mol %) |
|---------|----------------------------------|-------------------|--------------------|---------------|
| D7 | N-(4-methylcyclohexylidene)-2-methylaniline | o-nitrotoluene | 96.1 | 94.4 |
| D8 | N-(3-ethylcyclohexylidene)-4-methylaniline | p-nitrotoluene | 98.1 | 96.5 |
| D9 | N-(2-methylcyclohexylidene)-4-methylaniline | p-nitrotoluene | 99.7 | 98.5 |
| D10 | N-cyclohexylidene-3-ethylaniline | m-nitrotoluene | 98.8 | 95.9 |
| D11 | N-(4-methylcyclohexylidene)-4-methoxyaniline | 4-nitroanisole | 98.1 | 94.9 |
| D12 | N-(4-methylcyclohexylidene)-4-phenoxyaniline | 4-nitrodiphenylether | 98.2 | 95.3 |
| D13 | N-(4-methoxycyclohexylidene)-4-fluoroaniline | 4-fluoronitrobenzene | 90.6 | 89.1 |
| D14 | N-(4-methylcyclohexylidene)-4-hydroxyaniline | 4-nitrophenol | 96.0 | 93.7 |

EXAMPLE E1

In a 100 ml round bottom flask equipped with a reflux condenser with a separator, a thermometer and a stirrer were placed 1.86 g of 5% Pd/C containing 50% of water made by N.E. Chemcat Co., Ltd., 0.24 g of 1N-NaOH, 10 g of diethylene glycol dimethyl ether, 17.33 g (0.1 mol) of N-cyclohexylidene aniline and 8.29 g (0.067 mol) of nitrobenzene. Afterward, the reactor was heated up to 160° C. with stirring, and reaction was then carried out for 2 hours by maintaining the reactor at 158°–162° C. During this reaction, water present in the catalyst and water produced by the reaction were removed from the reaction system by adding benzene to the reactor to cause azeotropy, condensing water by the reflux condenser, and then separating it by the separator. The amount of the removed water was 2.6 g. Next, the reaction solution was cooled to room temperature, and the 5% Pd/C was then removed from the reaction solution by filtration. The resultant filtrate was analyzed by the use of gas chromatography. The conversion of an imine was 100%, and the yield of diphenylamine was 93.0%.

EXAMPLES E2 TO E8 AND COMPARATIVE EXAMPLES E1 TO E3

Reactions were carried out by the same procedure as in Example E1 except that diethylene glycol dimethyl ether in Example E1 was replaced with various polar solvents shown in Table 7.

The results are set forth in Table 7.

TABLE 7

| Example | Solvent | Cocatalyst | Conversion of Imine (mol %) | Yield of Diphenylamine (mol %) |
|---------|---------|------------|-----------------------------|-------------------------------|
| E2 | N,N-dimethylacetamide | NaOH | 100.0 | 94.2 |
| E3 | N,N'-dimethylimidazolidinone | NaOH | 100.0 | 93.5 |
| E4 | p-cresol | NaOH | 98.8 | 90.4 |
| E5 | N,N-dimethylformamide | NaOH | 100.0 | 92.8 |

TABLE 7-continued

| Example | Solvent | Cocatalyst | Conversion of Imine (mol %) | Yield of Diphenylamine (mol %) |
|---|---|---|---|---|
| E6 | Tetramethylurea | NaOH | 99.2 | 90.6 |
| E7 | N-methylpyrrolidone | NaOH | 98.4 | 89.7 |
| E8 | Methyl salicylate | NaOH | 99.6 | 92.2 |
| Comp. Ex. E1 | — | NaOH | 97.5 | 84.8 |
| Comp. Ex. E2 | — | — | 92.5 | 68.1 |
| Comp. Ex. E3 | p-tert-butyltoluene | NaOH | 91.1 | 67.4 |

EXAMPLES E9 AND E10

Reactions were carried out by the same procedure as in Example E1 except that in place of 0.24 g of 1N-NaOH in Example E1, an alkali metal compound and/or an alkaline earth metal compound shown in Table 8 was used as a co-catalyst.

The results are set forth together with those of Example E1 in Table 8.

TABLE 8

| Example | Cocatalyst Kind | Cocatalyst Amount* (wt %/Pd) | Conversion of Imine (mol %) | Yield of Diphenylamine (mol %) |
|---|---|---|---|---|
| E1 | NaOH | Na: 11.9 | 100.0 | 93.0 |
| E9 | Ca(OH)$_2$ | Ca: 20 | 100.0 | 92.3 |
| E10 | NaOH + Mg(OH)$_2$ | Na: 5 Mg: 12 | 100.0 | 93.0 |

*The amount of the cocatalyst in terms of an alkali metal and/or an alkaline earth metal.

EXAMPLE F1

In a 100 ml round bottom flask equipped with a reflux condenser with a separator, a thermometer and a stirrer were placed 2.57 g of 5% Pd/C containing 50% of water made by N.E. Chemcat Co., Ltd., 0.30 g of 1N-NaOH, 22.23 g of N,N-dimethylformamide, 20.51 g (0.1 mol) of N-(4-methylcyclohexylidene)-4-methylaniline and 9.24 g (0.067 mol) of p-nitrotoluene. Afterward, the reactor was heated up to 140° C. with stirring, and reaction was then carried out for 2 hours by maintaining the reactor at 138°–142° C. During this reaction, water present in the catalyst and water produced by the reaction were removed from the reaction system by adding benzene to the reactor to cause azeotropy, condensing water by the reflux condenser, and then separating it by the separator. The amount of the removed water was 3.6 g. Next, the reaction solution was cooled to room temperature, and the 5% Pd/C was then removed from the reaction solution by filtration. The resultant filtrate was analyzed by the use of gas chromatography. The conversion of an imine was 99.7%, and the yield of 4,4'-dimethyldiphenylamine was 90.9%.

COMPARATIVE EXAMPLE F1

Reaction was carried out by the same procedure as in Example F1 except that N,N-dimethylformamide was not used. As a result, the conversion of an imine was 46.6%, and the yield of 4,4'-dimethyldiphenylamine was 36.0%.

COMPARATIVE EXAMPLE F2

Reaction was carried out by the same procedure as in Example F1 except that 1N-NaOH and N,N-dimethylformamide were not used. As a result, the conversion of an imine was 45.3%, and the yield of 4,4'-dimethyldiphenylamine was 31.5%.

EXAMPLES F2 TO F6

Reactions were carried out by the same procedure as in Example F1 except that N,N-dimethylformamide in Example F1 was replaced with various polar solvents shown in Table 9 and reaction temperature was set to 160° C.

The results are set forth in Table 9.

TABLE 9

| Example | Solvent | Conversion of Imine (mol %) | Yield of Ditolylamine (mol %) |
|---|---|---|---|
| F2 | N,N'-dimethylimidazolidinone | 98.5 | 95.2 |
| F3 | p-cresol | 100.0 | 94.6 |
| F4 | Phenol | 99.3 | 90.6 |
| F5 | Diethylene glycol dimethyl ether | 98.7 | 93.1 |
| F6 | p-methoxyphenol | 98.8 | 94.1 |

EXAMPLES F7 AND F8

Reactions were carried out by the same procedure as in Example F1 except that in place of 0.3 g of 1N-NaOH in Example F1, an alkaline metal compound and/or an alkaline earth metal compound shown in Table 10 was used as a co-catalyst.

The results are set forth together with those of Example F1 in Table 10.

TABLE 10

| Example | Cocatalyst Kind | Cocatalyst Amount* (wt %/Pd) | Conversion of Imine (mol %) | Yield of Diphenylamine (mol %) |
|---|---|---|---|---|
| F1 | NaOH | Na: 10.7 | 99.7 | 90.9 |
| F7 | Ca(OH)$_2$ | Ca: 20 | 99.7 | 89.8 |
| F8 | NaOH + Mg(OH)$_2$ | Na: 5 Mg: 12 | 100.0 | 90.6 |

*The amount of the cocatalyst in terms of an alkali metal and/or an alkaline earth metal.

EXAMPLES F9 TO F16

Reactions were carried out by the same procedure as in Example F1 except that the combination of N-(4-methylcyclohexylidene)-4-methylaniline and p-nitrotoluene in Example F1 was changed to combinations of N-cyclohexylidene amino compounds and hydrogen acceptors shown in Table 11.

The results are set forth in Table 11.

TABLE 11

| Example | N-Cyclohexylidene-amino Compound | Hydrogen Acceptor | Conversion (mol %) | Yield (mol %) |
|---|---|---|---|---|
| F9 | N-(4-methylcyclohexylidene)-4-methylaniline | o-nitrotoluene | 97.9 | 94.0 |
| F10 | N-(3-ethylcyclohexylidene)-4-methylaniline | p-nitrotoluene | 98.3 | 95.2 |
| F11 | N-(2-methylcyclohexylidene)-4-methylaniline | p-nitrotoluene | 99.8 | 97.1 |
| F12 | N-cyclohexylidene-3-ethylaniline | m-nitrotoluene | 99.1 | 94.7 |
| F13 | N-(4-methylcyclohexylidene)-4-methoxyaniline | 4-nitroanisole | 98.5 | 93.5 |
| F14 | N-(4-methylcyclohexylidene)-4-phenoxyaniline | 4-nitrodiphenyl ether | 98.5 | 93.6 |
| F15 | N-(4-methoxycyclohexylidene)-4-fluoroaniline | 4-fluoronitrobenzene | 90.8 | 88.3 |
| F16 | N-(4-methylcyclohexylidene)-4-hydroxyaniline | 4-nitrophenol | 96.2 | 92.8 |

COMPARATIVE EXAMPLE F3

Reaction was carried out by the same procedure as in Example F9 except that N,N-dimethylformamide in Example F9 was not used. As a result, the conversion of an imine was 55.2%, and the yield of 4,2'-dimethyldiphenylamine was 42.3%.

COMPARATIVE EXAMPLE F4

Reaction was carried out by the same procedure as in Example F9 except that 1N-NaOH and N,N-dimethylformamide in Example F9 were not used. As a result, the conversion of an imine was 17.0%, and the yield of 4,2'-dimethyldiphenylamine was 12.5%.

COMPARATIVE EXAMPLE F5

Reaction was carried out by the same procedure as in Example F11 except that N,N-dimethylformamide in Example F11 was not used. As a result, the conversion of an imine was 48.2%, and the yield of 2,4'-dimethyldiphenylamine was 35.8%.

COMPARATIVE EXAMPLE F6

Reaction was carried out by the same procedure as in Example F11 except that 1N-NaOH and N,N-dimethylformamide in Example F11 were not used. As a result, the conversion of an imine was 11.3%, and the yield of 2,4'-dimethyldiphenylamine was 3.5%.

EXAMPLE G1

In a 100 ml round bottom flask equipped with a reflux condenser with a separator, a thermometer and a stirrer were placed 1.86 g of 5% Pd/C containing 50% of water made by N.E. Chemcat Co., Ltd., 0.24 g of 1N-NaOH, 17.33 g (0.1 mol) of N-cyclohexylideneaniline, 8.29 g (0.067 mol) of nitrobenzene. Afterward, the reactor was heated up to 160° C. with stirring, and reaction was then carried out for 3 hours by maintaining the reactor at 158°–162° C. During this reaction, water present in the catalyst and water produced by the reaction were removed from the reaction system by adding benzene to the reactor to cause azeotropy, condensing water by the reflux condenser, and then separating it by the separator. The amount of the removed water was 2.7 g. Next, the reaction solution was cooled to room temperature, and the 5% Pd/C was then removed from the reaction solution by filtration. The resultant filtrate was analyzed by the use of gas chromatography. The conversion of an imine was 99.4%, and the yield of diphenylamine was 86.7%.

Examples G2 to G10 and Comparative Example G1 Reactions were carried out by the same procedure as in Example G1 except that in place of 0.24 g of 1N-NaOH in Example G1, various kinds of cocatalysts were used in various amounts as shown in Table 12.

The results are set forth together with those of Example G1 in Table 12.

TABLE 12

| Example/ Comp. Example | Cocatalyst Kind | Amount* (wt %/Pd) | Conversion of Imine (mol %) | Yield of Diphenylamine (mol %) |
|---|---|---|---|---|
| Example G1 | NaOH | 11.9 | 99.4 | 86.7 |
| Example G2 | NaOH | 20 | 100.0 | 87.5 |
| Example G3 | Na$_2$CO$_3$ | 12 | 99.8 | 86.9 |
| Example G4 | NaHCO$_3$ | 12 | 99.0 | 86.0 |
| Example G5 | KOH | 6 | 100.0 | 87.6 |
| Example G6 | LiOH | 5 | 98.5 | 84.5 |
| Example G7 | Ca(OH)$_2$ | 20 | 97.7 | 83.9 |
| Example G8 | Mg(OH)$_2$ | 12 | 98.7 | 84.8 |
| Example G9 | NaOH + Ca(OH)$_2$ | Na: 10 Ca: 10 | 99.2 | 85.9 |
| Example G10 | KOH + Mg(OH)$_2$ | K: 5 Mg: 12 | 99.7 | 86.5 |
| Comp. Example G1 | — | — | 90.1 | 69.2 |

*The amount of the cocatalyst in terms of an alkali metal and/or an alkaline earth metal.

EXAMPLE H1

In a 100 ml round bottom flask equipped with a reflux condenser with a separator, a thermometer and a stirrer were placed 2.57 g of 5% Pd/C containing 50% of water made by N.E. Chemcat Co., Ltd., 0.30 g of 1N-NaOH, 20.51 g (0.1 mol) of N-(4-methylcyclohexylidene)-4-methylaniline and 9.24 g (0.067 mol) of p-nitrotoluene. Afterward, the reactor was heated up to 160° C. with stirring, and reaction was the carried out for 3 hours by maintaining the reactor at 158°–162° C. During this reaction, water present in the catalyst and water produced by the reaction were removed from the reaction system by adding benzene to the reactor to cause azeotropy, condensing water by the reflux condenser, and then separating it by the separator. The amount of the removed water was 3.0 g. Next, the reaction solution was cooled to room temperature, and the 5% Pd/C was then removed from the reaction solution by filtration. The resultant filtrate was analyzed by the use of gas chromatography. The conversion of an imine was 98.2%, and the yield of 4,4'-dimethyldiphenylamine was 85.5%.

EXAMPLES H2 TO H6

Reactions were carried out by the same procedure as in Example H1 except that in place of a cocatalyst in Example H1, various kinds of cocatalysts were used in various amounts as shown in Table 13.

The results are set forth together with those of Example H1 in Table 13.

TABLE 13

| Example | Cocatalyst Kind | Amount* (wt %/Pd) | Conversion of Imine (mol %) | Yield of Diphenylamine (mol %) |
|---|---|---|---|---|
| H1 | NaOH | 10.7 | 98.2 | 85.5 |
| H2 | NaOH | 20 | 98.6 | 86.7 |
| H3 | NaOH | 5 | 97.2 | 83.5 |
| H4 | NaHCO₃ | 12 | 98.2 | 85.1 |
| H5 | Ca(OH)₂ | 20 | 96.8 | 82.8 |
| H6 | NaOH + Ca(OH)₂ | Na: 10 Mg: 10 | 98.7 | 84.7 |

*The amount of the cocatalyst in terms of an alkali metal and/or an alkaline earth metal.

EXAMPLES H7 TO H14

Reactions were carried out by the same procedure as in Example H1 except that the combination of an N-cyclohexylidene amino compound and a hydrogen acceptor in Example H1 was changed to combinations shown in Table 14.

The results are set forth in Table 14.

TABLE 14

| Example | N-Cyclohexylidene-amino Compound | Hydrogen Acceptor | Conversion (mol %) | Yield (mol %) |
|---|---|---|---|---|
| H7 | N-(4-methylcyclohexylidine)-2-methylaniline | o-nitrotoluene | 95.2 | 85.3 |
| H8 | N-(3-ethylcyclohexylidene)-4-methylaniline | p-nitrotoluene | 98.3 | 88.6 |
| H9 | N-(2-methylcyclohexylidene)-4-methylaniline | p-nitrotoluene | 99.1 | 90.3 |
| H10 | N-cyclohexylidene-3-ethylaniline | m-nitrotoluene | 97.6 | 86.3 |
| H11 | N-(4-methylcyclohexylidene)-4-methoxyaniline | 4-nitroanisole | 97.9 | 87.2 |
| H12 | N-(4-methylcyclohexylidene)-4-phenoxyaniline | 4-nitrodiphenyl ether | 98.1 | 87.0 |
| H13 | N-(4-methoxycyclohexylidene)-4-fluoroaniline | 4-fluoronitrobenzene | 89.8 | 81.9 |
| H14 | N-(4-methylcyclohexylidene)-4-hydroxyaniline | 4-nitrophenol | 91.2 | 82.6 |

COMPARATIVE EXAMPLE H1

Reaction was carried out by the same procedure as Example H1 except that 1N-NaOH was not used. As a result, the conversion of an imine was 79.9%, and the yield of 4,4'-dimethyldiphenylamine was 66.8%.

COMPARATIVE EXAMPLE H2

Reaction was carried out by the same procedure as Example H7 except that 1N-NaOH was not used. As a result, the conversion of an imine was 61.3%, and the yield of 4,2'-dimethyldiphenylamine was 35.3%.

COMPARATIVE EXAMPLE H3

Reaction was carried out by the same procedure as Example H9 except that 1N-NaOH was not used. As a result, the conversion of an imine was 55.9%, and the yield of 4,2'-dimethyldiphenylamine was 34.1%.

EXAMPLE I1

In a 200 ml round bottom flask equipped with a reflux condenser with a separator, a thermometer and a stirrer were placed 5.59 g of 5% Pd/C containing 50% of water made by N.E. Chemcat Co., Ltd., 25.68 g of diethylene glycol dimethyl ether, 13.97 g (0.15 mol) of aniline, 29.44 g (0.3 mol) of cyclohexanone and 24.87 g (0.2 mol) of nitrobenzene. Afterward, the reactor was heated up to 160° C. with stirring, and reaction was then carried out for 3 hours by maintaining the reactor at 158°–162° C. Water present in the catalyst and water produced during this reaction was removed from the reaction system by adding benzene to the reactor to cause azeotropy, condensing water by the reflux condenser, and then separating it by the separator. The amount of the removed water was 12.4 g. Next, the reaction solution was cooled to room temperature, and the 5% Pd/C was then removed from the reaction solution by filtration. The resultant filtrate was analyzed by the use of gas chromatography. The conversion of cyclohexanone was 100%, and the yield of diphenylamine was 86.8%.

EXAMPLES I2 TO I8

Reactions were carried out by the same procedure as in Example I1 except that diethylene glycol dimethyl ether in Example I1 was replaced with various polar solvents shown in Table 15.

The results are set forth in Table 15.

TABLE 15

| Example | Solvent | Conversion of Imine (mol %) | Yield of Diphenylamine (mol %) |
|---|---|---|---|
| I2 | N,N-dimethylacetamide | 100.0 | 90.2 |
| I3 | N,N'-dimethylimidazolidinone | 98.9 | 86.2 |
| I4 | p-cresol | 100.0 | 91.7 |
| I5 | N,N-dimethylformamide | 100.0 | 91.4 |
| I6 | Tetramethylurea | 98.2 | 87.4 |
| I7 | N-methylpyrrolidone | 97.4 | 85.8 |

COMPARATIVE EXAMPLE I1

Reaction was carried out by the same procedure as in Example I1 except that diethylene glycol dimethyl ether was not used. As a result, the conversion of cyclohexanone was 96.6%, and the yield of diphenylamine was 76.3%.

COMPARATIVE EXAMPLE I2

Reaction was carried out by the same procedure as in Example I1 except that in place of diethylene glycol dimethyl ether, p-tert-butyltoluene was used as a solvent. As a result, the conversion of cyclohexanone was 91.1%, and the yield of diphenylamine was 67.3%.

EXAMPLE I8

Reaction was carried out by the same procedure as in Example I1 except that 32.39 g (0.39 mol) of cyclohexanone, 9.31 g (0.1 mol) of aniline and 24.62 g (0.2 mol) nitrobenzene were used. As a result, the yield of diphenylamine was 89.5%, and 1.8% of triphenylamine and 2.9% of N-cyclohexylaniline were produced.

EXAMPLE J1

In a 200 ml round bottom flask equipped with a reflux condenser with a separator, a thermometer and a stirrer were placed 7.72 g of 5% Pd/C containing 50% of water made by N.E. Chemcat Co., Ltd., 60.00 g of N,N-dimethylformamide, 16.07 g (0.15 mol) of p-toluidine, 33.65 g (0.3 mol) of 4-methylcyclohexanone and 27.43 g (0.2 mol) of p-nitrotoluene. Afterward, the reactor was heated up to 140° C. with stirring, and reaction was then carried out for 3 hours by maintaining the reactor at 134°–142° C. Water present in the catalyst and water produced during this reaction were removed from the reaction system by adding benzene to the reactor to cause azeotropy, condensing water by the reflux condenser, and then separating it by the separator. The amount of the removed water was 12.34 g. Next, the reaction solution was cooled to room temperature, and the 5% Pd/C was then removed from the reaction solution by filtration. The resultant filtrate was analyzed by the use of gas chromatography. The conversion of 4-methylcyclohexanone was 98.6%, and the yield of ditolylamine was 91.6%.

EXAMPLES J2 TO J7

Reactions were carried out by the same procedure as in Example J1 except that N,N-dimethylformamide in Example J1 was replaced with various polar solvents shown in Table 16 and reaction temperature was set to 160° C.

The results are set forth in Table 16.

TABLE 16

| Example | Solvent | Conversion (mol %) | Yield of Ditolylamine (mol %) |
|---|---|---|---|
| J2 | N,N-dimethylacetamide | 99.8 | 90.2 |
| J3 | N,N'-dimethylimidazolidinone | 98.9 | 89.2 |
| J4 | p-cresol | 100.0 | 94.3 |
| J5 | Diethylene glycol dimethyl ether | 98.0 | 89.4 |
| J6 | Tetramethylurea | 98.7 | 87.9 |
| J7 | N-methylpyrrolidone | 97.4 | 88.8 |

COMPARATIVE EXAMPLE J1

Reaction was carried out by the same procedure as in Example J1 except that N,N-dimethylformamide was not used. As a result, the conversion of 4-methylcyclohexanone was 51.6%, and the yield of ditolylamine was 7.9%.

COMPARATIVE EXAMPLE J2

Reaction was carried out by the same procedure as in Example J1 except that in place of N,N-dimethylformamide in Example J1, xylene was used as a solvent. As a result, the conversion of p-methylcyclohexanone was 53.7%, and the yield of ditolylamine was 9.0%.

EXAMPLES J8 TO J13

Reaction was carried out by the same procedure as in Example J1 except that the combination of p-toluidine, 4-methylcyclohexanone and p-nitrotoluene was replaced with materials shown in Table 17.

The results are set forth in Table 17.

TABLE 17

| Example | Cyclohexanone (nucleus-substituted compound) | Amine | Nitro-Compound | Desired Compound | Conversion (mol %) | Yield (mol %) |
|---|---|---|---|---|---|---|
| J8  | H₃C–⟨H⟩=O         | H₂N–⟨⟩–CH₃       | O₂N–⟨⟩–CH₃       | H₃C–⟨⟩–NH–⟨⟩–CH₃       | 97.1  | 90.7 |
| J9  | ⟨H⟩=O             | H₂N–⟨⟩–OCH₃      | O₂N–⟨⟩–OCH₃      | ⟨⟩–NH–⟨⟩–OCH₃          | 100.0 | 89.1 |
| J10 | H₃C–⟨H⟩=O         | CH₃-⟨⟩–NH₂       | CH₃-⟨⟩–NO₂       | H₃C–⟨⟩–NH–⟨⟩(CH₃)       | 99.5  | 87.1 |
| J11 | ⟨H⟩=O             | ⟨⟩–O–⟨⟩–NH₂      | ⟨⟩–O–⟨⟩–NO₂      | ⟨⟩–NH–⟨⟩–O–⟨⟩          | 99.6  | 90.0 |
| J12 | H₃C–⟨H⟩=O         | F–⟨⟩–NH₂         | F–⟨⟩–NO₂         | CH₃–⟨⟩–NH–⟨⟩–F         | 98.1  | 89.5 |
| J13 | H₃C–⟨H⟩=O         | HO–⟨⟩–NH₂        | HO–⟨⟩–NO₂        | CH₃–⟨⟩–NH–⟨⟩–OH        | 98.9  | 88.9 |

EXAMPLE K1

In a 200 ml round bottom flask equipped with a reflux condenser with a separator, a thermometer, a dropping device and a stirrer were placed 5.59 g of 5% Pd/C containing 50% of water made by N.E. Chemcat Co., Ltd., 25.68 g of diethylene glycol dimethyl ether and 13.97 g (0.15 mol) of aniline, and in the dropping device was prepared and stored a mixed solution of 29.44 g (0.3 mol) of cyclohexanone and 24.87 g (0.2 mol) of nitrobenzene. Afterward, the reactor was heated up to 160° C. with stirring, and after the removal of water present in the catalyst, the solution in the dropping device was dropped over 4 hours, while a temperature of 158°–162° C. was maintained. After completion of the dropping, the solution was stirred for 0.5 hour, while this temperature range was maintained. Water produced during this step was removed from the reaction system by adding benzene to the reactor to cause azeotropy, condensing water by the reflux condenser, and then separating it by the separator. The amount of the removed water was 12.6 g. Next, the reaction solution was cooled to room temperature, and the 5% Pd/C was then removed from the reaction solution by filtration. The resultant filtrate was analyzed by the use of gas chromatography. The conversion of cyclohexanone was 100%, and the yield of diphenylamine was 99.2%.

EXAMPLES K2 TO K8

Reactions were carried out by the same procedure as in Example K1 except that diethylene glycol dimethyl ether in Example K1 was replaced with various polar solvents shown in Table 18.

The results are set forth in Table 18.

TABLE 18

| Example | Solvent | Conversion (mol %) | Yield of Diphenylamine (mol %) |
|---|---|---|---|
| K2 | N,N-dimethylacetamide | 100.0 | 98.8 |
| K3 | N,N'-dimethylimidazolidinone | 100.0 | 98.5 |
| K4 | p-cresol | 98.9 | 97.1 |
| K5 | N,N-dimethylformamide | 100.0 | 99.1 |
| K6 | Tetramethylurea | 99.5 | 98.0 |
| K7 | N-methylpyrrolidone | 96.8 | 94.9 |
| K8 | Methyl salicylate | 98.7 | 96.8 |

COMPARATIVE EXAMPLE K1

Reaction was carried out by the same procedure as in Example K1 except that in place of diethylene glycol dimethyl ether in Example K1, p-tert-butyltoluene was used as a solvent. As a result, the conversion of cyclohexanone was 77.5%, and the yield of diphenylamine was 48.5%.

EXAMPLE L1

In a 200 ml round bottom flask equipped with a reflux condenser with a separator, a thermometer, a dropping device and a stirrer were placed 7.72 g of 5% Pd/C containing 50% of water made by N.E. Chemcat Co., Ltd., 60.00 g of N,N-dimethylformamide and 16.07 g (0.15 mol) of p-toluidine, and in the dropping device was prepared and stored a mixed solution of 33.65 g (0.3 mol) of 4-methylcyclohexanone and 27.43 g (0.2 mol) of p-nitrotoluene. Afterward, the reactor was heated up to 140° C. with stirring, and after the removal of water present in the catalyst, the solution in the dropping device was dropped over 6 hours, while a temperature of 134°–142° C. was maintained. After completion of the dropping, the solution was stirred for 1 hour, while this temperature range was kept up. Water produced during this step was removed from the reaction system by adding benzene to the reactor to cause azeotropy, condensing water by the reflux condenser, and then separating it by the separator. The amount of the removed water was 12.5 g. Next, the reaction solution was cooled to room temperature, and the 5% Pd/C was then removed from the reaction solution by filtration. The resultant filtrate was analyzed by the use of gas chromatography. The conversion of 4-methylcyclohexanone was 99.6%, and the yield of ditolylamine was 97.7%.

EXAMPLES L2 TO L7

Reactions were carried out by the same procedure as in Example L1 except that N,N-dimethylformamide in Example L1 was replaced with various polar solvents shown in Table 19 and reaction temperature was set to 160° C.

The results are set forth in Table 19.

TABLE 19

| Example | Solvent | Conversion (mol %) | Yield of Ditolylamine (mol %) |
|---|---|---|---|
| L2 | N,N-dimethylacetamide | 99.7 | 97.1 |
| L3 | N,N'-dimethylimidazolidinone | 99.1 | 96.5 |
| L4 | p-cresol | 99.9 | 98.1 |
| L5 | Diethylene glycol dimethyl ether | 98.0 | 96.1 |
| L6 | Tetramethylurea | 99.2 | 97.1 |
| L7 | N-methylpyrrolidone | 98.7 | 96.9 |

EXAMPLES L8 TO L13

Reactions were carried out by the same procedure as in Example L1 except that p-toluidine, 4-methylcyclohexanone and p-nitrotoluene in Example L1 were replaced with various materials shown in Table 20.

The results are set forth in Table 20.

TABLE 20

| Example | Cyclohexanone (nucleus-substituted compound) | Amine | Nitro-Compound | Desired Compound | Conversion (mol %) | Yield (mol %) |
|---|---|---|---|---|---|---|
| L8 | 4-methylcyclohexanone | H$_2$N–C$_6$H$_4$–CH$_3$ | O$_2$N–C$_6$H$_4$–CH$_3$ | H$_3$C–C$_6$H$_4$–NH–C$_6$H$_4$–CH$_3$ | 98.2 | 95.1 |
| L9 | cyclohexanone | H$_2$N–C$_6$H$_4$–OCH$_3$ | O$_2$N–C$_6$H$_4$–OCH$_3$ | C$_6$H$_5$–NH–C$_6$H$_4$–OCH$_3$ | 99.8 | 97.8 |
| L10 | 4-methylcyclohexanone | 2-CH$_3$–C$_6$H$_4$–NH$_2$ | 2-CH$_3$–C$_6$H$_4$–NO$_2$ | H$_3$C–C$_6$H$_4$–NH–C$_6$H$_4$–CH$_3$ | 99.6 | 96.8 |
| L11 | cyclohexanone | C$_6$H$_5$–O–C$_6$H$_4$–NH$_2$ | C$_6$H$_5$–O–C$_6$H$_4$–NO$_2$ | C$_6$H$_5$–NH–C$_6$H$_4$–O–C$_6$H$_5$ | 99.8 | 98.8 |
| L12 | 4-methylcyclohexanone | F–C$_6$H$_4$–NH$_2$ | F–C$_6$H$_4$–NO$_2$ | CH$_3$–C$_6$H$_4$–NH–C$_6$H$_4$–F | 98.9 | 96.7 |
| L13 | 4-methylcyclohexanone | HO–C$_6$H$_4$–NH$_2$ | HO–C$_6$H$_4$–NO$_2$ | CH$_3$–C$_6$H$_4$–NH–C$_6$H$_4$–OH | 99.3 | 96.9 |

EXAMPLE M1

In a 200 ml round bottom flask equipped with a reflux condenser with a separator, a thermometer and a stirrer were placed 7.72 g of 5% Pd/C containing 50% of water made by N.E. Chemcat Co., Ltd., 0.91 g of 1N-NaOH (Na content= 10.8 wt %/Pd), 60.00 of N,N-dimethylformamide, 16.07 g (0.15 mol) of p-toluidine, 33.65 g (0.3 mol) of 4-methylcyclohexanone and 27.43 g (0.2 mol) of p-nitrotoluene. Afterward, the reactor was heated up to 140° C. with stirring, and reaction was then carried out for 3 hours by maintaining the reactor at 138°–142° C. water present in the catalyst and water produced during this reaction were removed from the reaction system by adding benzene to the reactor to cause azeotropy, condensing water by the reflux condenser, and then separating it by the separator. The amount of the removed water was 15.22 g. Next, the reaction solution was cooled to room temperature, and the 5% Pd/C was then removed from the reaction solution by filtration. The resultant filtrate was analyzed by the use of gas chromatography. The conversion of 4-methylcyclohexanone was 99.8%, and the yield of ditolylamine was 94.2%.

EXAMPLE M2

In a 300 ml round bottom flask equipped with a reflux condenser with a separator, a thermometer, a dropping device and a stirrer were placed 4.66 g of 5% Pd/C containing 50% of water made by N.E. Chemcat Co., Ltd., 1.21 g of 1N-NaOH, 0.33 g of butyric acid, 42.80 g of diethylene glycol dimethyl ether and 23.28 g (0.25 mol) of aniline, and in the dropping device was prepared and stored a mixed solution of 49.07 g (0.5 mol) of cyclohexanone and 41.45 g (0.33 mol) of nitrobenzene. The reactor was heated to 160° C. with stirring, and after the removal of water present in the catalyst, the solution in the dropping device was dropped over 4 hours, while a temperature of 158°–162° C. was maintained. After completion of the dropping, the solution was stirred for 0.5 hour, while this temperature range was kept up. Water produced during this step was removed from the reaction system by adding benzene to the reactor to cause azeotropy, condensing water by the reflux condenser, and then separating it by the separator. The amount of the removed water was 21.0 g. Next, the reaction solution was cooled to room temperature, and the 5% Pd/C was then removed from the reaction solution by filtration. The resultant filtrate was analyzed by the use of gas chromatography. The conversion of cyclohexanone was 100%, and the yield of diphenylamine was 99.9%.

In succession, the previously recovered catalyst was used, and 5% Pd/C containing 50% of water, NAOH and butyric acid were added as shown in Table 21 and reaction was then similarly carried out. As a result, the average amount of the added new 5% Pd/C catalyst necessary to maintain a reaction rate and a selectivity was about 3% of its initial amount.

TABLE 21

| Number of Recycling | Amount of Added New Catalyst 5% Pd/C (g) | 1N–NaOH (g) | Butyric Acid (g) | Conversion (mol %) | Selectivity (mol %) |
|---|---|---|---|---|---|
| 1 | — | — | 0.33 | 100.0 | 99.8 |
| 2 | — | — | 0.33 | 100.0 | 99.7 |
| 3 | — | — | 0.33 | 100.0 | 99.7 |
| 4 | — | — | 0.33 | 100.0 | 99.1 |
| 5 | 0.70 | 0.18 | 0.33 | 100.0 | 99.7 |
| 6 | — | — | 0.33 | 99.7 | 98.6 |
| 7 | 0.47 | 0.12 | 0.33 | 100.0 | 99.5 |
| 8 | — | — | 0.33 | 100.0 | 99.0 |
| 9 | — | — | 0.33 | 98.7 | 97.3 |
| 10 | 0.23 | 0.06 | 0.33 | 100.0 | 99.3 |

EXAMPLE M3

In a 300 ml round bottom flask equipped with a reflux condenser with a separator, a thermometer, a dropping device and a stirrer were placed 4.66 g of 5% Pd/C containing 50% of water made by N.E. Chemcat Co., Ltd., 42.80 g of diethylene glycol dimethyl ether and 23.28 g (0.25 mol) of aniline, and in the dropping device was prepared and stored a mixed solution of 49.07 g (0.5 mol) of cyclohexanone and 41.45 g (0.33 mol) of nitrobenzene. Afterward, the reactor was heated up to 160° C. with stirring, and after the removal of water present in the catalyst, the solution in the dropping device was dropped over 4 hours, while a temperature of 158°–162° C. was maintained. After completion of the dropping, the solution was stirred for 0.5 hour, while this temperature range was maintained. Water produced during this step was removed from the reaction system by adding benzene to the reactor to cause azeotropy, condensing water by the reflux condenser, and then separating it by the separator. The amount of the removed water was 21.0 g. Next, the reaction solution was cooled to room temperature, and the 5% Pd/C was then removed from the reaction solution by filtration. The resultant filtrate was analyzed by the use of gas chromatography. The conversion of cyclohexanone was 100%, and the yield of diphenylamine was 99.2%.

In succession, the previously recovered catalyst was used, and 5% Pd/C was added as shown in Table 22 and the reaction was then similarly carried out. As a result, the average amount of the added new 5% Pd/C catalyst necessary to maintain a reaction rate and a selectivity was about 15% of its initial amount.

TABLE 22

| Number of Recycling | Amount of Added New 5% Pd/C Catalyst (g) | Conversion (mol %) | Selectivity (mol %) |
| --- | --- | --- | --- |
| 1 | 0.47 | 98.7 | 96.7 |
| 2 | 0.47 | 94.5 | 92.4 |
| 3 | 0.93 | 95.7 | 93.3 |
| 4 | 0.93 | 96.0 | 93.7 |
| 5 | 0.93 | 96.2 | 94.0 |
| 6 | 0.47 | 93.6 | 90.8 |
| 7 | 0.70 | 95.3 | 92.6 |
| 8 | 0.70 | 94.1 | 91.7 |
| 9 | 0.70 | 93.4 | 91.2 |
| 10 | 0.70 | 92.7 | 90.4 |

EXAMPLE N1

In a 200 ml round bottom flask equipped with a reflux condenser with a separator, a thermometer, a dropping device and a stirrer were placed 7.72 g of 5% Pd/C containing 50% of water made by N.E. Chemcat Co., Ltd., 0.91 g of 1N-NaOH, 0.55 g of butyric acid, 60.00 g of N,N-dimethylformamide and 16.07 g (0.15 mol) of toluidine, and in the dropping device was prepared and stored a mixed solution of 33.65 g (0–3 mol) of 4-methylcyclohexanone and 27.43 g (0.2 mol) of p-nitrotoluene. Afterward, the reactor was heated up to 140° C. with stirring, and after the removal of water present in the catalyst, the solution in the dropping device was dropped over 6 hours, while a temperature of 134°–142° C. was maintained. After completion of the dropping, the solution was stirred for 1 hour, while this temperature range was maintained. Water produced during this step was removed from the reaction system by adding benzene to the reactor to cause azeotropy, condensing water by the reflux condenser, and then separating it by the separator. The amount of the removed water was 12.6 g. Next, the reaction solution was cooled to room temperature, and the 5% Pd/C was then removed from the reaction solution by filtration. The resultant filtrate was analyzed by the use of gas chromatography. The conversion of 4-methylcyclohexanone was 99.8%, and the yield of ditolylamine was 98.8%.

In succession, the previously recovered catalyst was used, and 5% Pd/C containing 50% of water, NAOH and butyric acid were added as shown in Table 23 and the reaction was then similarly carried out. As a result, the average amount of the added new catalyst necessary to maintain a reaction rate and a selectivity was about 6.0% of its initial amount.

TABLE 23

| Number of Recycling | Amount of Added New Catalyst 5% Pd/C (g) | 1N–NaOH (g) | Butyric Acid (g) | Conversion (mol %) | Selectivity (mol %) |
| --- | --- | --- | --- | --- | --- |
| 1 | 0.39 | 0.08 | 0.55 | 100.0 | 99.2 |
| 2 | 0.19 | 0.08 | 0.55 | 100.0 | 99.1 |
| 3 | 0.19 | 0.08 | 0.55 | 100.0 | 99.0 |
| 4 | 0.19 | 0.08 | 0.55 | 100.0 | 99.1 |
| 5 | 0.19 | 0.08 | 0.55 | 100.0 | 98.9 |

EXAMPLE N2

In a 200 ml round bottom flask equipped with a reflux condenser with a separator, a thermometer, a dropping device and a stirrer were placed 7.72 g of 5% Pd/C containing 50% of water made by N.E. Chemcat Co., Ltd., 60.00 g of N,N-dimethylformamide and 16.07 g (0.15 mol) of toluidine, and in the dropping device was prepared and stored a mixed solution of 33.65 g (0.3 mol) of 4-methylcyclohexanone and 27.43 g (0.2 mol) of p-nitrotoluene. Afterward, the reactor was heated up to 140° C. with stirring, and after the removal of water present in the catalyst, the solution in the dropping device was dropped over 6 hours, while a temperature of 134°–142° C. was maintained. After completion of the dropping, the solution was stirred for 1 hour, while this temperature range was maintained. Water produced during this step was removed from the reaction system by adding benzene to the reactor to cause azeotropy, condensing water by the reflux condenser, and then separating it by the separator. The amount of the removed water was 12.5 g. Next, the reaction solution was cooled to room temperature, and the 5% Pd/C was then removed from the reaction solution by filtration. The resultant filtrate was analyzed by the use of gas chromatography. The conversion of 4-methylcyclohexanone was 99.6%, and the yield of ditolylamine was 98.7%.

In succession, the previously recovered catalyst was used, and the new catalyst was added as much as an average amount of about 8.3% based on the initial amount as shown in Table 24 and the reaction was then similarly carried out. The results obtained were shown in the same table.

TABLE 24

| Number of Recycling | Amount of Added New Catalyst 5% Pd/C (g) | Conversion (mol %) | Selectivity (mol %) |
| --- | --- | --- | --- |
| 1 | 0.39 | 98.5 | 96.7 |
| 2 | 0.19 | 95.6 | 92.8 |
| 3 | 0.39 | 95.8 | 92.7 |
| 4 | 0.39 | 93.9 | 89.9 |
| 5 | 0.59 | 95.1 | 90.5 |

The method of the further aspect of the present invention will hereinafter be described specifically by the following examples.

EXAMPLE O1

Charged in a 200-ml round bottom flask equipped with a separator-fitted reflux condenser, a thermometer and a stirrer were 3.03 g of 5% Pd/C (water content: 50 wt. %; product of N.E. Chemcat Corp.), 64.0 g of N,N-dimethylacetamide, 7.21 g (0.07 mole) of paraphenylenediamine (hereinafter abbreviated as "PPD"), 19.63 g (0.20 mole) of cyclohexanone (hereinafter abbreviated as "CH") and 18.42 g (0.13 mole) of paranitroaniline (hereinafter abbreviated as "PNA"). While maintaining the internal temperature at 158°–162° C., the contents were continuously stirred for 5 hours. During that period, benzene was charged so that resulting water was azeotropically distilled off. The azeotropically distilled water-benzene mixture was condensed in the reflux condenser and was then separated through the separator. The reaction mixture was then cooled to room temperature and the 5% Pd/C was filtered off from the reaction mixture. The filtrate was analyzed by gas chromatography, thereby obtaining the following data:

Conversion of CH: 99.95 (mol % per CH)

Yield of P-ADPA: 49.87 (mol per CH)

By-production of N,N'-p-DPPA: 36.50 (mol % per CH)

Recovery of non-dehydrogenated product: 3.26 (mol % per CH)

EXAMPLES O2–O4

In each example, a reaction was conducted in a similar manner to Example O1 except that the amount of PPD in Examples O2–O4 was changed as shown in Table 25. The results are presented in Table 25.

COMPARATIVE EXAMPLE 1

A reaction was conducted in a similar manner to Example O1 except for the substitution of p-cymene for N,N-dimethylacetamide in Example O1. The results are presented in Table 25.

TABLE 25

|  | (PPD + PNA)/CH (molar ratio) | Conversion of CH (mol %) | Yield of p-ADPA (mol %) | By-production of N,N'-p-DPPA | Recovery of un-dehydrogenated product (mol %) |
|---|---|---|---|---|---|
| Example O2 | 1.4 | 100 | 72.57 | 14.21 | 5.14 |
| Example O3 | 1.7 | 100 | 75.18 | 10.67 | 5.53 |
| Example O4 | 2.0 | 99.93 | 79.51 | 7.13 | 5.06 |
| Comp. Ex. O1 | 1.0 | 100 | 28.70 | 1.27 | 45.98 |

EXAMPLE O5

Charged in a 200-ml round bottom flask equipped with a separator-fitted reflux condenser, a thermometer, a dropping device and a stirrer were 3.03 g of 5% Pd/C (water content: 50 wt. %; product of N.E. Chemcat Corp.), 40.0 g of N,N-dimethylacetamide, and 7.21 g (0.07 mole) of PPD. A mixed solution consisting of 19.63 g (0.20 mole) of CH and 18.42 g (0.13 mole) of PNA was prepared and charged in the dropping device. The internal temperature of the flask was raised to 160° C. under stirring and, while maintaining the internal temperature at 158°–162° C., the solution in the dropping device was added dropwise over 6 hours. After the completion of the dropwise addition, the contents of the flask were stirred for 1 hour while maintaining the internal temperature within the above temperature range. During that period, benzene was charged so that resulting water was azeotropically distilled off. The azeotropically distilled water-benzene mixture was condensed in the reflux condenser and was then separated through the separator. The reaction mixture was then cooled to room temperature and the 5% Pd/C was filtered off from the reaction mixture. The filtrate was analyzed by gas chromatography, thereby obtaining the following data:

Conversion of CH: 99.51 (mol % per CH)

Yield of P-ADPA: 54.00 (mol % per CH)

By-production of N,N'-p-DPPA: 35.65 (mol % per CH)

Recovery of non-dehydrogenated product: 9.72 (mol % per CH)

EXAMPLES O6–O7 & COMPARATIVE EXAMPLE O2

In each example, a reaction was conducted in a similar manner to Example O5 except that the corresponding polar solvent (Examples O6 and O7) or the non-polar solvent (Comparative Example O2) shown in Table 26 was used instead of N,N-dimethylacetamide in Example O5. The results are presented in Table 26.

TABLE 26

|  | Solvent | Conversion of CH (mol %) | Yield of p-ADPA (mol %) | By-production of N,N'-p-DPPA | Recovery of un-dehydrogenated product (mol %) |
|---|---|---|---|---|---|
| Example O6 | 1,3-Dimethyl-imidazolidinone | 100 | 56.56 | 29.13 | 9.49 |
| Example O7 | Diethylene glycol dimethyl ether | 100 | 57.51 | 32.75 | 4.37 |
| Comp. Ex. O2 | p-Cymene | 100 | 32.13 | 1.36 | 48.98 |

EXAMPLES O8–O12

In each example, a reaction was conducted in a similar manner to Example O5 except that the amount of PPD in Examples O5 was changed to set the (PPD+PNA)/CH ratio at the corresponding value shown in Table 27.

The results are presented in Table 27.

TABLE 27

|  | (PPD + PNA) /CH (molar ratio) | Conversion of CH (mol %) | Yield of p-ADPA (mol %) | By-production of N,N'-p-DPPA | Recovery of un-dehydrogenated product (mol %) |
|---|---|---|---|---|---|
| Example O8 | 1.187 | 100 | 75.12 | 22.90 | 2.91 |
| Example O9 | 1.437 | 100 | 81.03 | 16.16 | 2.19 |
| Example O10 | 1.687 | 100 | 86.87 | 0.67 | 1.71 |
| Example O11 | 1.987 | 100 | 89.64 | 9.12 | 1.24 |
| Example O12 | 6.950 | 100 | 92.99 | 1.66 | 5.65 |

EXAMPLES O13–O15

In each example, a reaction was conducted in a similar manner to Example O5 except that PPD and PNA in Example O5 were replaced by metaphenylenediamine (hereinafter abbreviated as "MPD") and metanitroaniline (hereinafter abbreviated as "MNA"), respectively, and the (MPD+MNA)/CH ratio was set at the corresponding value shown in Table 28.

The results are presented in Table 28.

TABLE 28

|  | (MPD + MNA) /CH (molar ratio) | Conversion of CH (mol %) | Yield of m-ADPA (mol %) | By-production of N,N'-p-DPPA | Recovery of un-dehydrogenated product (mol %) |
|---|---|---|---|---|---|
| Example O13 | 1.000 | 99.9 | 53.4 | 43.2 | 0.9 |
| Example O14 | 1.417 | 99.9 | 75.0 | 18.5 | 1.3 |
| Example O15 | 1.917 | 100 | 81.8 | 12.4 | 0.7 |

EXAMPLE O16

Charged in a 200-ml round bottom flask equipped with a separator-fitted reflux condenser, a thermometer, a dropping device and a stirrer were 3.03 g of 5% Pd/C (water content: 50 wt. %; product of N.E. Chemcat Corp.), 40.0 g of triethylene glycol dimethyl ether, and 27.04 g (0.25 mole) of orthophenylenediamine. A mixed solution consisting of 19.63 g (0.20 mole) of CH and 18.42 g (0.13 mole) of orthonitroaniline was prepared and charged in the dropping device. The internal temperature of the flask was raised to 170° C. under stirring and, while maintaining the internal temperature at 170°–173° C., the solution in the dropping device was added dropwise over 15 hours. After the completion of the dropwise addition, the contents of the flask were stirred for 2 hours while maintaining the internal temperature within the above temperature range. During that period, benzene was charged so that resulting water was azeotropically distilled off. The azeotropically distilled water-benzene mixture was condensed in the reflux condenser and was then separated through the separator. The reaction mixture was then cooled to room temperature and the 5% Pd/C was filtered off from the reaction mixture. The filtrate was analyzed by gas chromatography, thereby obtaining the following data:

Conversion of CH: 100 (mol % per CH)

Yield of O-ADPA: 63.8 (mol % per CH)

Recovery of non-dehydrogenated product: 35.8 (mol % per CH)

What is claimed is:

1. A method for preparing an aromatic secondary amino compound represented by the formula (2)

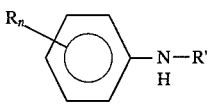

wherein each R is a hydrogen atom, alkyl group, alkoxy group, amino group, hydroxyl group or fluorine; R' is an alkyl group, phenyl group, benzyl group, naphthyl group, furyl group, furfuryl group or cyclohexyl group, and R' may be substituted by an alkyl group, alkoxy group, phenyl group, phenoxy group, cyclohexyl group, amino group, substituted amino group, carboxyl group, hydroxyl group or fluorine; and n is an integer of from 0 to 5 which comprises the step of reacting cyclohexanone or a nucleus-substituted cyclohexanone represented by the formula (3)

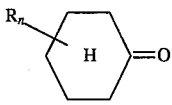
(3)

wherein R is defined above,
an amine represented by the formula (4)

R'—NH$_2$ (4)

wherein R' is defined above, and
a nitro compound as a hydrogen acceptor corresponding to the amine and represented by the formula (5)

R'—NO$_2$ (5)

wherein R' is defined above in a sulfur-free polar solvent at a temperature in the range of from 120° to 250° C. in the presence of a catalyst selected from the noble metals of Group VIII of the Periodic Table.

2. The method for preparing an aromatic secondary amino compound according to claim 1 wherein said reaction is carried out by dropping cyclohexanone or the nucleus-substituted cyclohexanone and the nitro compound into the sulfur-free polar solvent in which the hydrogen moving catalyst is dispersed.

3. The method for preparing an aromatic secondary amino compound according to claim 1 wherein said reaction is carried out by adding an alkaline metal compound and/or an alkaline earth metal compound as a cocatalyst.

4. The method for preparing an aromatic secondary amino compound according to claim 3 wherein said reaction is carried out by dropping cyclohexanone or the nucleus-substituted cyclohexanone and the nitro compound into a mixture obtained by adding the cocatalyst and the hydrogen moving catalyst to the sulfur-free polar solvent.

5. The method for preparing an aromatic secondary amino compound according to claim 3 wherein an organic acid having a logarithm (pKa) of a reciprocal of an acid dissociation constant in the range of from 3.5 to 6.0 is further added.

6. The method for preparing an aromatic secondary amino compound according to claim 4 wherein an organic acid having a logarithm (pKa) of a reciprocal of an acid dissociation constant in the range of from 3.5 to 6.0 is further added to the sulfur-free polar solvent.

7. A process for the preparation of aminodiphenylamine, which comprises reacting phenylenediamine and cyclohexanone in the presence of a hydrogen transfer catalyst in a sulfur-free polar solvent while using nitroaniline as a hydrogen acceptor.

8. A process according to claim 7, wherein the reaction is conducted while adding nitroaniline and cyclohexanone dropwise into a liquid mixture of the hydrogen transfer catalyst, phenylenediamine and the sulfur-free polar solvent.

* * * * *